(12) United States Patent
Kajiyama et al.

(10) Patent No.: US 11,707,261 B2
(45) Date of Patent: Jul. 25, 2023

(54) ULTRASOUND PROBE ENABLED FOR ULTRASOUND RECEPTION OPERATION OF AT LEAST TWO MODES

(71) Applicant: FUJIFILM Healthcare Corporation, Kashiwa (JP)

(72) Inventors: Shinya Kajiyama, Kashiwa (JP); Yoshihiro Hayashi, Kashiwa (JP); Shinta Takano, Kashiwa (JP)

(73) Assignee: FUJIFILM Healthcare Corporation, Chiba (JP)

( * ) Notice: Subject to any disclaimer, the term of this patent is extended or adjusted under 35 U.S.C. 154(b) by 0 days.

(21) Appl. No.: 17/506,288

(22) Filed: Oct. 20, 2021

(65) Prior Publication Data
US 2022/0125413 A1    Apr. 28, 2022

(30) Foreign Application Priority Data
Oct. 22, 2020    (JP) .............................. JP2020-177100

(51) Int. Cl.
*A61B 8/08*    (2006.01)
*A61B 8/00*    (2006.01)

(52) U.S. Cl.
CPC ............ *A61B 8/488* (2013.01); *A61B 8/4488* (2013.01); *A61B 8/54* (2013.01)

(58) Field of Classification Search
CPC ......... A61B 8/4488; A61B 8/54; A61B 8/488; A61B 8/5246; G01S 15/8979; B06B 1/0622; B06B 1/0607
See application file for complete search history.

(56) References Cited

U.S. PATENT DOCUMENTS

| 4,141,347 A * | 2/1979 | Green ................. G01S 7/52084 600/455 |
| 4,145,931 A * | 3/1979 | Tancrell .............. G01S 15/8918 73/626 |
| 4,528,854 A * | 7/1985 | Shimazaki .......... G01N 29/262 367/105 |
| 5,349,960 A * | 9/1994 | Gondo ................ G01S 15/8979 600/455 |

(Continued)

FOREIGN PATENT DOCUMENTS

| DE | 102018103258 A1 * | 8/2019 | ........... B06B 1/0622 |
| JP | 2011-142931 A | 7/2011 | |

OTHER PUBLICATIONS

DE-102018103258-A1 (Year: 2019).*

*Primary Examiner* — Joel Lamprecht
*Assistant Examiner* — Nyrobi Celestine
(74) *Attorney, Agent, or Firm* — Paul Teng

(57) ABSTRACT

A two-dimensional array ultrasound probe, which is enabled for ultrasonic reception operation of a continuous wave Doppler mode (C mode) and an imaging mode (B mode). The probe includes a reception circuit provided for each transducer and a first multiplexer; a plurality of first wires connected to the first multiplexer; a second wire connected to a plurality of first wires outside the array; switches that are provided to the second wire and that can be turned off to adapt to phasing addition units; a plurality of second multiplexers connected to the second wire and a plurality of first output ports for the first mode; and a plurality of second output ports that are connected to each region between the switches on the second wire and that are used in the second mode.

16 Claims, 11 Drawing Sheets

(56) References Cited

U.S. PATENT DOCUMENTS

| | | | | |
|---|---|---|---|---|
| 5,351,690 A * | 10/1994 | Okada | G01S 7/52095 | 73/609 |
| 5,520,186 A * | 5/1996 | Deitrich | G01S 15/8918 | 600/447 |
| 5,555,534 A * | 9/1996 | Maslak | G01S 15/8979 | 367/7 |
| 5,897,501 A * | 4/1999 | Wildes | A61B 8/4494 | 600/447 |
| 6,126,602 A * | 10/2000 | Savord | G01S 15/8925 | 600/443 |
| 6,142,946 A * | 11/2000 | Hwang | A61B 8/4472 | 600/459 |
| 6,241,675 B1 * | 6/2001 | Smith | G01S 15/8993 | 600/443 |
| 2004/0267126 A1 * | 12/2004 | Takeuchi | G10K 11/346 | 600/447 |
| 2004/0267135 A1 * | 12/2004 | Takeuchi | G01S 15/8925 | 600/459 |
| 2005/0243812 A1 * | 11/2005 | Phelps | G01S 7/5208 | 370/360 |
| 2006/0241464 A1 * | 10/2006 | Ohtake | G01S 15/8927 | 600/457 |
| 2007/0016052 A1 * | 1/2007 | Fukukita | A61B 8/56 | 600/459 |
| 2007/0236374 A1 * | 10/2007 | Brueske | G01S 7/5208 | 341/143 |
| 2008/0146930 A1 * | 6/2008 | Takeuchi | A61B 8/4494 | 600/447 |
| 2009/0171213 A1 * | 7/2009 | Savord | G01S 7/5208 | 600/447 |
| 2011/0077517 A1 * | 3/2011 | Satou | A61B 8/4477 | 600/443 |
| 2011/0172537 A1 | 7/2011 | Hongou et al. | | |
| 2012/0095344 A1 * | 4/2012 | Kristoffersen | G03B 42/06 | 600/447 |
| 2015/0080724 A1 * | 3/2015 | Rothberg | G03B 27/52 | 600/440 |
| 2015/0099977 A1 * | 4/2015 | Kim | G01S 15/8925 | 600/447 |
| 2015/0241397 A1 * | 8/2015 | Savord | G01N 29/24 | 600/459 |
| 2015/0297183 A1 * | 10/2015 | Freeman | G01S 7/5208 | 600/459 |
| 2017/0071579 A1 * | 3/2017 | Ko | A61B 8/4483 | |
| 2017/0074978 A1 * | 3/2017 | Miller | G01S 7/52084 | |
| 2018/0341011 A1 * | 11/2018 | Hashimoto | G01S 7/52017 | |

* cited by examiner

ULTRASOUND PROBE ENABLED FOR ULTRASOUND RECEPTION OPERATION OF AT LEAST TWO MODES

CROSS REFERENCE TO RELATED APPLICATION

This application claims priority to Japanese Patent Application No. 2020-177100 filed on Oct. 22, 2020, which is incorporated herein by reference in its entirety including the specification, claims, drawings, and abstract.

TECHNICAL FIELD

This description discloses a technique related to an ultrasound probe, in particular, a technique related to a two-dimensional array ultrasound probe.

BACKGROUND

An ultrasound probe is a component of an ultrasonic diagnostic apparatus, for example. In recent years, the development of an ultrasonic diagnostic apparatus that can produce three-dimensional images has been progressing. For three-dimensional imaging, a plurality of ultrasonic transducers in an ultrasound probe need to be arranged in a two-dimensional array. There are various ways of transmitting and receiving ultrasonic signals (which may also be described as modes) using a two-dimensional array ultrasound probe such as an imaging mode what is called B mode and the continuous wave Doppler mode. In the continuous wave Doppler mode, this probe processes continuous wave Doppler reception signals from each transducer. It should be noted that transducers, and circuits and signal lines connected to them may be collectively referred to as a transducer channel. In the B mode, this probe performs, for example, phasing addition of a plurality of reception signals. Phasing is adjusting the phase by delay.

An example of prior art related to a two-dimensional array ultrasound probe is JP 2011-142931 A. JP 2011-142931 A discloses an ultrasound probe in which the number of signal lines in the probe cable is reduced while a wide dynamic range in the continuous wave Doppler mode is ensured.

In the configuration of the two-dimensional array ultrasound probe, the number of transducers mounted therein increases by the square of the conventional one-dimensional array ultrasound probe. However, it is difficult to increase, with an increase in the number of transducers by the square, the number of cables (corresponding signal lines) connecting the probe and the main unit. Therefore, one of the countermeasures is to reduce, in the circuits in the probe, the large number of reception signals to output to a smaller number of reception signals by phasing addition, so that they can be transmitted to the main unit through a smaller number of cables. To realize such a configuration, it is necessary to implement functions such as ultrasound transmission/reception and phasing addition in a circuit such as an IC mounted on the probe. In this circuit, each transducer needs to be provided with a transmission/reception circuit or the like supporting the function of the corresponding transducer. The number of transducers in a two-dimensional array is, for example, as many as several thousands to 10,000 or more. In this case, a large number of transmission/reception circuits for the large number of transducers need to be mounted in the IC. In each reception circuit, the number of reception signals needs to be reduced according to the number of Output cables by phasing addition. Achieving these presents the challenge of, for example, upsizing the circuits mounted in the two-dimensional array ultrasound probe and high-density packaging.

On the other hand, in the two-dimensional array ultrasound probe in the continuous wave Doppler mode, the IC in the array tends to consume a lot of power because it needs to constantly transmit continuous waves. In particular, when the size of the IC circuit is large or when many active circuits such as amplifiers are used, the power consumption increases. The increase in the power consumption leads to heat generation by the probe. Since the probe is used for a living body surface, significant heat generation may cause burns.

The aforementioned two-dimensional array ultrasound probe may have an advanced function that can support both the continuous wave Doppler mode and other modes such as the B mode. However, the prior art has problems in circuit size, power consumption, and the like as mentioned above, and therefore leaves room for studies in order to overcome these problems.

It is an advantage of the ultrasound probe disclosed in this description to provide a technique that is related to a two-dimensional array ultrasound probe, achieves reception operation in at least two modes: the continuous wave Doppler mode and another mode, and can reduce the circuit size and power consumption.

SUMMARY

A representative embodiment of the ultrasound probe disclosed in this description has the following configuration, An ultrasound probe of the embodiment includes a plurality of transducers arranged in a two-dimensional array. The ultrasound probe is enabled for ultrasonic reception operation of at least two modes: a first mode, which is a continuous wave Doppler mode, and a second mode, which is a mode other than the continuous wave. Doppler mode. When the direction of one dimension of the two-dimensional array is the first direction, and the direction of the other dimension is the second direction, the ultrasound probe includes: a reception circuit that is provided for each of the plurality of transducers; a first multiplexer that is provided to be connected to each reception circuit; a plurality of first wires that are provided to be connected to the first multiplexer and extend in the first direction; outside the two-dimensional array, a second wire that is provided to be connected to the plurality of first wires and extend in the second direction; switches that are provided to the second wire and can be turned off to adapt to the units of phasing addition of reception signals of the plurality of transducers; a plurality of second multiplexers that are connected to the second wire; a plurality of first output ports that are connected to the plurality of second multiplexers and used in the first mode; and a plurality of second output ports that are connected to each region between the switches on the second wire and are used in the second mode.

With a representative embodiment of the ultrasound probe disclosed in this description, in relation to a technique that is related to a two-dimensional array ultrasound probe, reception operation in at least two modes: the continuous wave Doppler mode and another mode can be performed, and the circuit size and power consumption can be reduced. Problems, configurations, effects, and the like other than the aforementioned ones will be described in DESCRIPTION OF EMBODIMENTS.

BRIEF DESCRIPTION OF DRAWINGS

Embodiments of the present disclosure will be described based on the following figures, wherein.

DESCRIPTION OF EMBODIMENTS

Figure 1:
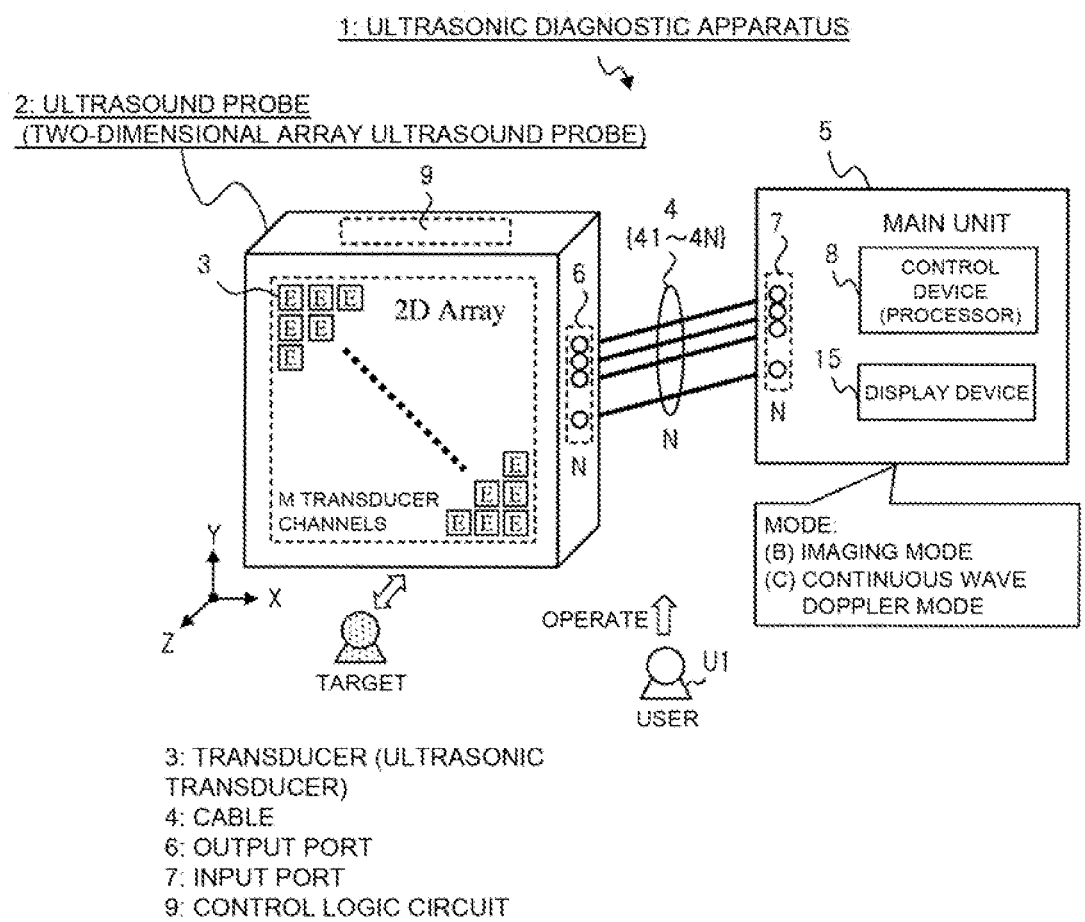
FIG. 1 shows an example of the configuration of an ultrasonic diagnostic apparatus including a probe (two-dimensional array ultrasound probe) of Embodiment 1.

Embodiments of the ultrasound probe disclosed in this description will be now described in detail with reference to the attached drawings. In the drawings, the same components are denoted by the same reference numerals, and overlapping description will be omitted. The embodiments are merely illustrative, and some description will be omitted as appropriate. The ultrasound probe disclosed in this description can be implemented in various other forms. Unless otherwise specified, each component may be one or more than one. If there are plurality of identical or similar components, they may be denoted by the same reference numeral but with different subscripts. For easy understanding, the representation of the components in the drawings may not represent the actual position, size, shape, range, and the like, and each ultrasound probe disclosed in this description is not necessarily limited by the position, size, shape, range, and the like disclosed in the drawings. In addition, although the data and information for identifying various components are expressed with identification information, identifiers, IDs, names, numbers, and the like, these expressions are interchangeable.

Although, for convenience of explanation, the processing by a program may be expressed considering the program, function, processor, or the like as a main part, the main part as hardware for them is, for example, a processor or a controller, device, computer, or system including a processor. The computer executes processing according to the program read into the memory, using resources such as a memory and a communication interface as appropriate through the processor. As a result, predetermined functions, processing units, and the like are implemented. Each processor includes semiconductor devices such as a CPU and GPU. Each processor includes devices and circuits capable of predetermined operations. The processing is not limited to software program processing but can also be implemented in a dedicated circuit. An FPGA, ASIC, or the like can be used as the dedicated circuit. The program may be pre-installed as data on the target computer, or may be distributed and installed as data from the program source to the target computer. The program source may be a program distribution server on the communication network or a on-transitory computer-readable storage medium. The program may consist of a plurality of program modules.

Problem and Other Matters

A supplementary explanation of the problem and other matters will now be given. With the ultrasonic diagnostic apparatus, simple operation of placing the ultrasound probe on the surface of a target (for example, a living body) allows real-time observation and display of the state of a target region, for example, a beating heart and a fetus's action. In the ultrasonic diagnostic apparatus, the probe and the main unit are connected through a cable or the like. The main unit is used for, for example, control, diagnosis, and display. The ultrasonic diagnostic apparatus transmits ultrasound into the target by supplying high-voltage drive signals to each of ultrasonic transducers of the probe, and receives the reflected waves of the ultrasound generated by the difference in acoustic impedance in the target. The probe transmits a plurality of reception signals through a plurality of transducer channels to the main unit via a cable or the like. The main unit performs processing based on the reception signals, and generates and displays images and the like for observation.

The imaging mode (sometimes referred to as B mode) is a mode in which one scanning line is obtained by one transmission/reception to obtain an image by raster scanning. In the B mode, the following operations are performed, for example. The probe drives a plurality of transducers with an independent delay when transmitting ultrasound, thereby focusing an acoustic pulse to a desired part of the target (i.e., a focus point). This action is called beam forming and beam scanning of ultrasound. When receiving ultrasound, to compensate the difference in the distance from the reflection point to each transducer, the probe gives an independent delay to the plurality of transducers to coherently align the phases of the signals and add them up. Such an operation is called phasing addition.

The continuous wave Doppler mode (which may be referred to gas C mode) is a mode for transmitting and receiving continuous waves using the Doppler effect. The continuous wave Doppler mode is, for example, used for measuring time fluctuations in blood flow rate in circulation organs. In the C mode, the following operations are performed, for example. The two-dimensional array ultrasound probe constantly transmits continuous waves using half of the transducers of the array, and constantly receives reflected waves with the other half of the transducers. The continuous waves are reflected in the blood flow, causing a frequency shift due to the Doppler effect. The probe receives a signal on which this frequency shift component is superimposed.

The ultrasonic diagnostic apparatus that can produce three-dimensional images improves inspection efficiency by specifying an arbitrary cross section from the three-dimensional image and obtaining a cross-sectional image. For three-dimensional imaging, the ultrasound probe includes a two-dimensional array of transducers. In this array configuration, an increased large number of transducers are used as described above, thereby requiring a large number of cables (corresponding signal lines) used to connect the probe and the main unit. To deal with this, in the circuit configuration, the large number of reception signals to be output are reduced to a smaller number of reception signals in the circuits in the probe by phasing addition, or the like and transmitted to the main unit through the corresponding number of cables from the probe. To achieve this configuration it is necessary to implement functions, such as ultrasound transmission/reception each transducer and the aforementioned phasing addition (i.e., reduction of the number of signals), in circuits such as ICs mounted on the array in the probe. However, in this configuration, as described above, a large number of circuits are needed corresponding to a large number of transducers (for example, thousands to 10,000 or more) in a two-dimensional array, as well as active circuits such as amplifiers and delay circuits, which increases the circuit size and power consumption.

To resolve this problem, the two-dimensional array ultrasound probe of the embodiment has a circuit configuration enabled for operation of reception of ultrasonic signals in at least two modes: the continuous wave Doppler mode and another mode such as the B mode, so that the circuit size and power consumption of the circuit configuration can be reduced. In the embodiment, as a proposal of the circuit configuration, a configuration is employed in which, in the B mode, a plurality of reception signals are subjected to phasing addition upon reception operation, while in the C mode, upon reception operation, phasing addition is performed not in the probe but in the main unit. With this configuration, the power consumed for reception operation at the probe can be significantly reduced. In particular, low-noise amplifiers that amplify the signals received from the transducers and delay circuits used for phasing addition are active circuits with relatively high power consumption. This circuit configuration minimizes use of such active circuits or uses no active circuits to drastically reduce its power consumption. In other words, if the circuit configuration of the probe is configured to process and output a large number of reception signals from a large number of transducers through passive circuits such as electric power such as a switch and a multiplexer with low power consumption, the power consumption can be drastically reduced. In particular, if a circuit configuration that outputs through only passive circuits can be achieved, the power consumption of the probe can be even made almost zero.

However, even in the continuous wave Doppler mode, it may be necessary to transmit and receive ultrasound continuous waves in the form of a beam generated by a certain level of convergence, to a focal point at a desired point (for example, the back low position of the valve of the heart) of the target by beamforming (i.e., directional transmission/reception). In this case, the probe needs a circuit for receiving the beam. For example, in the circuits of the main unit, besides demodulation of continuous wave Doppler shift components based on reception signals from the probe, phasing addition is performed. To achieve this, the two-dimensional array ultrasound probe needs preprocessing for discriminating the phases of the plurality of reception signals. For this reason, the two-dimensional array ultrasound probe of the embodiment has a circuit configuration that can discriminate the phases upon reception operation involving beamforming in the C mode.

In summary, the two-dimensional array ultrasound probe of the embodiment has an efficient circuit configuration that can achieve both reduction of the number of signals in the B mode by phasing addition, and phase discrimination in the C mode.

Note that JP 2011-142931 A also discloses a circuit configuration of a two-dimensional array ultrasound probe in which reception operation can be switched between the continuous wave Doppler mode and the other mode. JP 2011-142931 A discloses that reception operation can be switched by controlling: a matrix switch 1044 shown in FIG. 1. This matrix switch 1044 receives outputs from each transducer and selects the outputs in phase with each other. In addition, under switching control, reception signals from each transducer pass through a delay circuit in modes other than the continuous wave Doppler mode, and bypass the delay circuit in the continuous wave Doppler mode.

However, considering the implementation of a circuit including such a matrix switch in a two-dimensional array ultrasound probe with a large number of transducers, the circuit size increases, which makes physical implementation difficult. With this circuit configuration, all transducer channels in the array and all reception channels of the main unit must be connected by all possible regression via a matrix switch. In other words, a target transducer channel and a target receiving channel must be connected under switching control by the matrix switch.

With this circuit configuration, if the number of transducer channels in the array is M and the number of output ports in the array and the number of reception channels in the main unit is N, simply a large number of (M×N) switches must be installed in the probe. Besides, N wires must be provided for each transducer channel in the probe. For instance, when M is 10,000 and N is 200, the required number of switches is 2 million. Implementation of such a large number of switches and wiring in a probe is not practical. JP 2011-142931 A does not mention an implementation method for reducing switches and wiring in the aforementioned circuit configuration. The embodiment includes an idea for the implementation method for reducing switches and wiring.

The following problems can also arise. In the circuit configuration of the aforementioned two-dimensional array ultrasound probe, in the continuous wave Doppler mode involving beamforming, the number of transducer channels connected to each output port from which reception signals are output may not be equal; that is, may be different or unequal. For instance, when, in accordance with a smaller number of output ports, a plurality of reception signals (especially phase-discriminated signals) of a plurality of transducer channels are combined into signals for each output port, the difference in the numbers of signals to be combined between the output ports may become significant. The main unit generates, for example, an image of time fluctuations in blood flow rate from the plurality of reception signals input/received at the plurality of input ports (the reception channels described above) from the plurality of output ports of the probe via the cables. At that time, if there is such difference or inequality, the brightness of the image may vary unnecessarily depending on the focus point in beamforming. This viewpoint is not disclosed in the prior art.

Considering these problems, the two-dimensional array ultrasound probe of the embodiment has a circuit configuration that is enabled for reception operation in the two modes described above. The circuit configuration is different from a circuit configuration in which a matrix switch establishes connection by all possible regression as in JP 2011-142931 A, and can be practically implemented, and its circuit size and power consumption can be reduced. This probe has a circuit configuration that can support both phasing addition (reduction of the number of signals) in the B mode and phase discrimination in the C mode involving beamforming. In the circuit configuration of this probe, the circuit area, the number of elements, the number of wires, and the like are reduced and passive circuits are used, minimizing use of active circuits. Further, in the circuit configuration of this probe, the number of transducer channels connected to each output port (i.e., the number of reception signals to be combined into one) can be made equal.

To be specific, the probe of the embodiment has a circuit configuration including a hierarchical switch structure in and out of the array, in which a plurality of reception signals of a plurality of transducer channels are grouped into a plurality of phasing addition units and output from a plurality of output ports in the B mode, and are phase-discriminated into a plurality of phase discrimination units according to a plurality of phases of the continuous wave Doppler without undergoing phasing addition and output from the plurality of output ports in the C mode. Moreover, with the circuit configuration, the number of transducer channels connected to each output port can be controlled to be equal in the C mode.

Embodiment 1

A two-dimensional array ultrasound probe of Embodiment 1 of the ultrasound probe disclosed in this description will now be described with reference to FIGS. 1 to 5. The two-dimensional array ultrasound probe of Embodiment 1 has functions that enable reception operation in at least two modes: the function of performing reception operation in the continuous wave Doppler mode (C mode) which involves beamforming; and the function of performing reception operation in the imaging mode (B mode) which is a mode other than the continuous wave Doppler mode. The continuous wave Doppler mode is also referred to as a first mode, and the imaging mode is also referred to as a second mode.

A two-dimensional array ultrasound probe 2 of Embodiment 1 shown in FIG. 1 and other drawings has, in the circuit configuration, regarding a correlation between M transducer channels and N output ports 6 (corresponding to input ports 7 of the main unit) a hierarchical switch structure in and out of the array instead of a switch structure that establishes (M×N) all possible regression connections. To be specific, this structure includes, M the array, first multiplexers 102 (FIG. 4) each disposed for the corresponding transducer channel, and a plurality of first wires 103 connected to the first multiplexer 102 and extending in a first direction, and, out of the array, second wires 104 connected to the plurality of first wires 103 and extending in a second direction, a plurality of switches 105 disposed on the second wires 104, a plurality of second multiplexers 108 connected to the second wires 104, first output ports 107 connected to the second multiplexers 108, and a plurality of second output ports 106 each connected to a portion between switches 105 on the same second wire 104.

In such a circuit configuration, for a plurality of reception signals of a plurality of transducers 3, the probe 2 in the first mode controls the first multiplexers 102, the switches 105, and the second multiplexers 108, sorting the signals into a plurality of groups according to phase discrimination of a plurality of phases, and in the second mode, controls the first multiplexers 102, the switches 105, and the second multiplexers 108 so as to divide them into a plurality of phasing addition units.

[1-1. Ultrasonic Diagnostic Apparatus]

FIG. 1 shows an example configuration of an ultrasonic diagnostic apparatus 1 including the probe 2 which is the two-dimensional array ultrasound probe of Embodiment. 1. The ultrasonic diagnostic apparatus 1 includes the probe 2 which is a two-dimensional array ultrasound probe, and a main unit 5, which are connected to each other through a medium such as cables 4. The probe 2 includes a plurality of (M) transducers 3 arranged in a two-dimensional array. The ultrasonic diagnostic apparatus 1 has at least two modes: the first mode that is the continuous wave Doppler mode (C mode); and the second mode that is the imaging mode (B mode), and switches between them as appropriate. The 13 mode is an example of a mode other than the C mode, which is not necessarily the B mode.

The probe 2 includes a plurality of (N) output ports 6, and the main unit 5 has a plurality of (N) input ports 7 corresponding to them. Multiple (N) output ports 6 translate into output terminals, transmission ports, and transmission channels. Multiple (N) input ports 7 translate into input terminals, reception ports, and reception channels.

The cable 4 includes a plurality of (N) cables 41, 42, 4N that connect the plurality of (N) output ports 6 to the plurality of (N) input ports 7 on a one-to-one basis. The cables 4 translate into signal lines or communication lines. Note that the plurality of (N) cables 4 may be bound into one cable 4. Although one-to-one connection is adopted in this example, this is not necessarily the case, and one may have more ports than another one.

Note that the probe 2 of Embodiment 1 is particularly characterized by its circuit configuration related to ultrasound reception operation. The reception operation will therefore be mainly described below. In relation to the reception operation, the output ports 6 are parts for outputting and transmitting reception signals, and the input ports 7 are parts for inputting and receiving the reception signals. Each port and cable 4 can also be used for transmission operation. If that is the case, the output ports 6 function as input ports, and the input ports 7 function as output ports. A modification can be made so that the circuit configuration related to transmission operation and reception operation and the cable 4 are separated.

The main unit 5 includes a control device (i.e., processor) 8, a display device 15, and the like. The control device 8 controls the probe 2 by transmitting and receiving signals to/from the probe 2, and has the function of, for example, analyzing signals and generating images. The control device 8 controls switching between two modes according to user U1's operation and settings, and the like. The main unit 5 also includes an input device and the like not shown in the drawing. A display device 15 or other devices may be built in or externally connected to the main unit 5. The main unit 5 may be composed of a dedicated device, or a general-purpose computer such as a PC and software. The user U1 operates the main unit 5 and the probe 2. The user U1 can observe the target portion while checking the images and information shown on the display screen of the display device 15.

The probe 2 has a circuit including an IC (integrated circuit) besides a plurality of (M) transducers 3 arranged in a two-dimensional array (i.e., a matrix). This circuit includes elements and wires which will be described below, and a control logic circuit 9. The control logic circuit 9 controls the transmission/reception circuit and the like of the plurality of transducers 3 of the probe 2 according to control by the control device 8 of the main unit 5. The control logic circuit 9 controls switching or selected state of elements such as multiplexers and switches, which will be described later.

Note that FIG. 1 shows the X, Y, and Z directions as explanatory directions. The X and Y directions are the two directions constituting the two-dimensional array of the probe 2. The Y direction corresponding to one dimension is the first direction, and the direction X corresponding to the other dimension is the second direction. The Z direction is perpendicular to the direction X and the Y direction. The Y direction is the direction in which the columns extend, and the direction X is the direction in which the rows extend.

As shown in FIG. 1, in a main array area 220 (FIG. 2) of the probe 2, a plurality of transducer channels 201 (FIG. 2) including the plurality of transducers 3 and the transmission/reception circuits for each transducer 3 are arranged in a two-dimensional array. A wire 202 (FIG. 2) connected to each transducer channel 201 of the main array area 220 and the circuit elements constituting the output port 6 and the like are located and implemented in an outer area 230 (FIG. 2) which is outer in relation to the array area 220. Hence, this circuit configuration of the probe 2 contributes to reductions in the circuit size and power consumption, thereby achieving high-density packaging.

[1-2. Two-Dimensional Array Ultrasound Probe]

Figure 2:
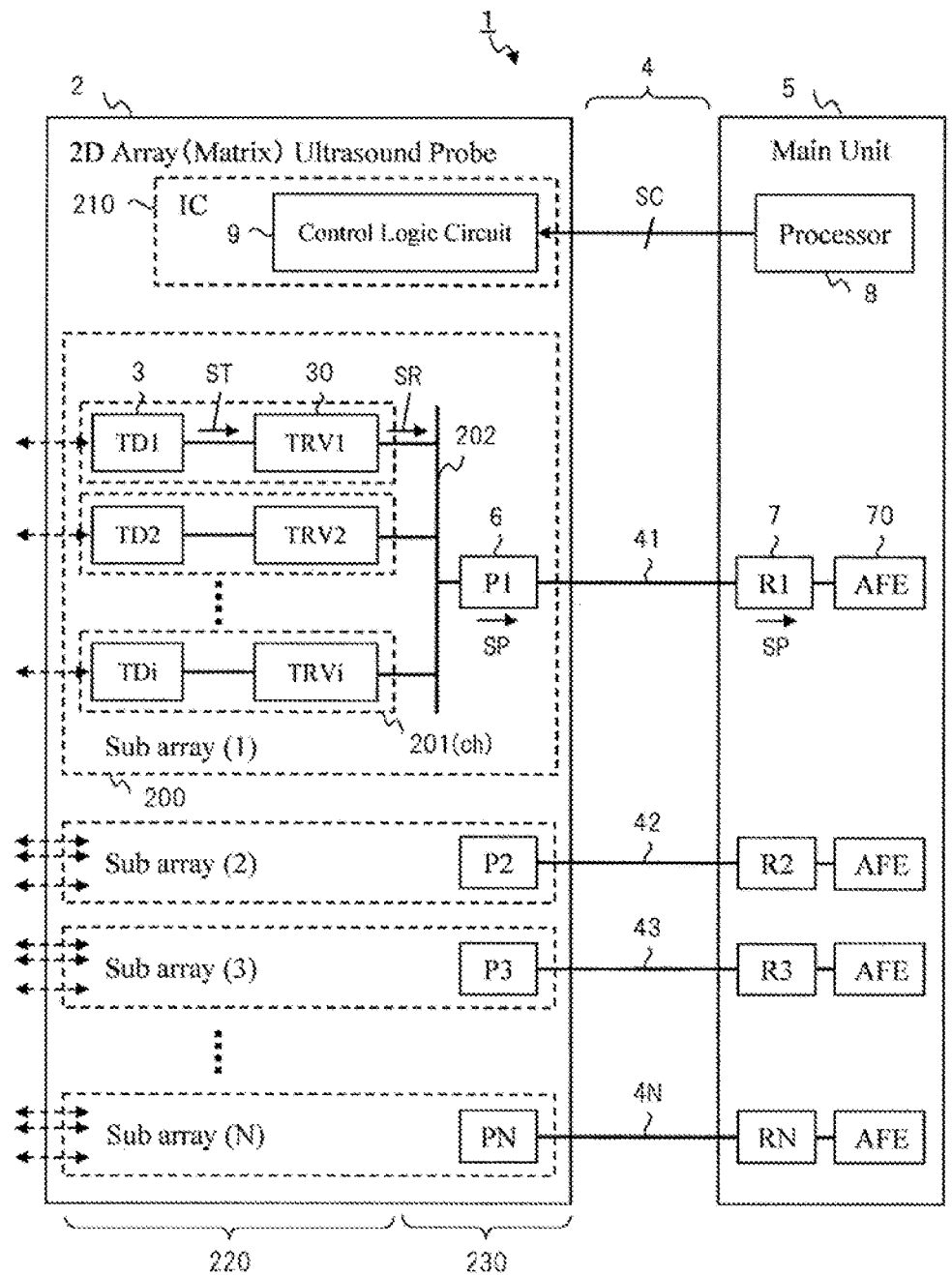
FIG. 2 shows an example of the configuration of connection between the probe of Embodiment 1 and a main unit.

FIG. 2 shows an example configuration of the connection between the probe 2 and the main unit 5. FIG. 2 also shows an example configuration of a sub-array 200 that adapts to the phasing addition units in the imaging mode (B mode). The plurality of (M) transducers 3 in the probe 2 are divided into a plurality of sub-arrays 200 during grouping into phasing addition units in the B mode. One sub-array 200 is a group consisting of a plurality of (for example, i) transducers 3 and transducer channels 201 of the transmission/reception circuits 30.

The plurality of (M) reception signals (ST, SR) at the plurality of (M) transducers 3 are combined into a smaller number of reception signals (SP) according to the number (N) of output ports 6 by phasing addition in the B mode. The plurality of (i) reception signals (ST, SR) at one sub-array 200 are combined into one reception signal (SP).

A transmission/reception circuit 30 is provided for each transducer 3 in the probe 2. A portion composed of a transducer 3 and a transmission/reception circuit 30 is referred to as a transducer channel 201. Upon reception operation in the B mode, the reception signal ST at a transducer 3 undergoes processing such as phasing in the reception circuit of the transmission/reception circuit 30 and is output as a reception signal SR The plurality of (i) reception signals SR at a sub-array 200 are added together through the wire 202 into one reception signal SP, which is output from one output port 6. Similarly, a plurality of (N) reception signals SP are output from a plurality of (N) output ports 6 (P1 to PN) of a plurality of (N) sub-arrays 200 of the probe 2. The plurality of (N) reception signals SP are transmitted to the plurality of (N) input ports 7 (R1 to RN) of the main unit 5 through a plurality of (N) cables 4 (41 to 4N). In this way, a large number of (M) reception signals are combined into a smaller number of (N) reception signals (that is, the number of signals is reduced), so that the number of required cables 4 is reduced.

The main unit 5 includes a reception circuit (analog front end) 70 for each input port 7. The reception circuit 70 processes the reception signal SP. In the continuous wave Doppler mode, the reception circuit 70 performs processing such as demodulation and phasing. It should be noted that the input port 7 and the reception circuit 70 may be integrally formed in one piece.

As various types of control in the ultrasonic diagnostic apparatus 1, the control device 8 in the main unit 5 controls mode switching and the like based on program processing and the like. The control device 8 transmits the generated control signal SC to the control logic circuit 9 in an IC 210 of the probe 2 through a predetermined signal line in the cable 4. The control logic circuit 9 controls the plurality of transducers 3 and transmission/reception circuits 30 of the probe 2 in response to the control signal SC according to the mode. This control includes the control of switching between transmission and reception at the plurality of transducers 3 of the probe 2, the control of the delay for ultrasonic focusing by beamforming, and the control of switching between phasing addition units and phase discrimination units described later. In the B mode, the control logic circuit 9 controls assignment and switching of phasing addition units for the switches and registers. In the C mode, the control logic circuit 9 controls assignment and switching of phase discrimination units for the switches and registers. The control logic circuit 9 sets and stores control information in the registers for these types of control.

In the example configuration shown in FIG. 2, the control device 8 of the main unit 5 mainly performs various types of control on the probe 2. Such a configuration is not always adopted. For example, the control logic circuit 9 of the probe 2 may be mainly used to perform various types of control (such as mode switching). Various types of control and signal processing may be performed by either the control device 8 of the main unit 5 or the control logic circuit 9 of the probe 2. In addition, although the probe 2 and the main unit 5 are separated in the example configuration shown in FIG. 2, this is not necessarily the case, and the prole 2 and the main unit 5 may be integrally formed into one piece.

Further, in the example configuration shown in FIG. 2, addition (which is also referred to as synthesis, superimposition, modulation, unification, and the like) of a plurality of reception signals is achieved by connecting a plurality of transducer channels 201 to the same wire 202. This is not necessarily the case, and the addition of a plurality of signals may be achieved by using a circuit such as an adder, a multiplier, or a modulator.

[1-3. Transmission/Reception Circuit]

Figure 3:
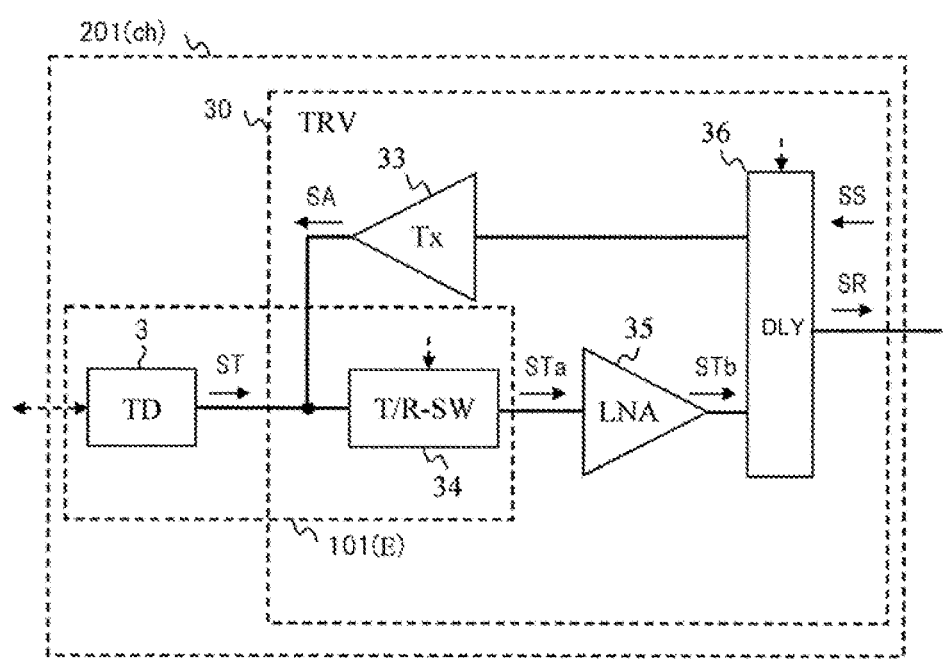
FIG. 3 shows an example of the basic configuration of a transmission/reception circuit of the probe of Embodiment 1.

FIG. 3 shows the basic configuration of the transmission/reception circuit 30 of one transducer channel 201. The transmission/reception circuit 30 for each transducer 3 includes a transmission circuit 33, a transmission/reception separation switch 34, a reception low noise amplifier 35 (LNA), and a micro delay circuit 36. For ultrasonic transmission operation, the micro delay circuit 36 and the transmission circuit 33 are used. For ultrasonic reception operation, the transmission/reception separation switch 34, the reception low noise amplifier 35, and the micro delay circuit 36 are used. The wire from the transducer 3 is branched and connected to the transmission circuit 33 and the transmission/reception separation switch 34. The wire from the transmission/reception separation switch 34 is connected to the reception low noise amplifier 35. The transmission circuit 33 and the reception low noise amplifier 35 are connected to the micro delay circuit 36.

The transmission circuit 33 is composed of, for example, a high-voltage MOS, generates a signal SA which is a high-voltage drive signal based on a signal from the micro delay circuit 36 based on a transmission signal SS, and drives the transducer 3 with the signal SA. Hence, ultrasound is transmitted from the transducer 3 to the target. In the case of the pulsar method, the transmission circuit 33 corresponds to a pulsar.

The transmission/reception separation switch 34 is switched between the on state and off state according to switching control by the control logic circuit 9. During transmission operation, the transmission/reception separation switch 34 is forced in the off state, and the transducer 3 is separated from the transmission circuit 33 and the reception low noise amplifier 35 in order to protect the reception low noise amplifier 35 and the like serving as low-voltage reception circuits from the signal SA, which is a high-voltage drive signal. During reception operation, the transmission/reception separation switch 34 is forced in the on state, and the transducer 3 and the reception low noise amplifier 35 are connected so that a weak reception signal ST can pass from the transducer 3.

Upon reception operation in the C mode, the probe 2 halts the reception low noise amplifier 35 and the micro delay circuit 36 so that the reception signal (ST and STa) from the transducer 3 is output as the reception signal SR of the transducer channel 201 without being amplified or delayed.

In Embodiment 1, upon reception operation in the B mode, the reception signal is amplified and delayed in the reception low noise amplifier 35 and the micro delay circuit 36 and then is output, and upon reception operation in the C mode, the reception low noise amplifier 35 and the micro delay circuit 36 are halted to pass the signal without being processed. As a result, during the reception operation in the C mode, in the probe 2, reception-related active circuits such as the reception low noise amplifier 35 are not used, so that the power consumption can be reduced. The reception circuit 70 in the main unit 5 performs processing such as amplification and delaying in response to the reception signal SR.

The reception low noise amplifier 35 in the low-voltage reception circuit amplifies the reception signal STa from the transducer 3 and outputs it as a reception signal STb to the micro delay circuit 36. Upon transmission operation, the micro delay circuit 36 performs beamforming by delaying the phase of the transmission signal SS. Upon reception operation, the micro delay circuit 36 performs phasing by delaying the phase of the reception signal STb, and outputs it as the reception signal SR.

In the example configuration shown in FIG. 3, active circuits such as the reception low noise amplifier 35 and the micro delay circuit 36 are provided in the transmission/reception circuit 30 of the probe 2, and are used properly according to the mode and operation. This is not necessarily the case: active circuits such as the reception low noise amplifier 35 and the micro delay circuit 36 may be provided in the reception circuit 70 of the main unit 5 instead of the transmission/reception circuit 30 of the probe 2. If that is the case, the circuit size of the probe 2 can be further reduced. It should be noted that the reception circuit 101 shown in FIG. 4 and other drawings described later corresponds to the transducer 3 and the transmission/reception separation switch 34 in FIG. 3. In Embodiment 1, specifically, the reception signal ST of the transducer 3 during the reception operation is output from the output port 6 according to the circuit configuration shown in FIG. 4 and other drawings described later.

In Embodiment 1, for example, the target area can be subjected to beamforming the C mode. Upon beamforming, a plurality of transmission signals from a plurality of transducers 3 are adjusted with a phase delay. This adjustment uses the micro delay circuit 36 shown in FIG. 3.

An object of Embodiment 1, for example, is to reduce the circuit size and power consumption of the probe 2. To achieve this, in the C mode, the transmission/reception circuit 30 of the probe 2 outputs the reception signal without phasing using a phase delay in the micro delay circuit 36 but with phasing with a phase delay in the reception circuit 70 in the main unit 5. The specific circuit configuration for this is shown below.

[1-4. C Mode]

Figure 4:
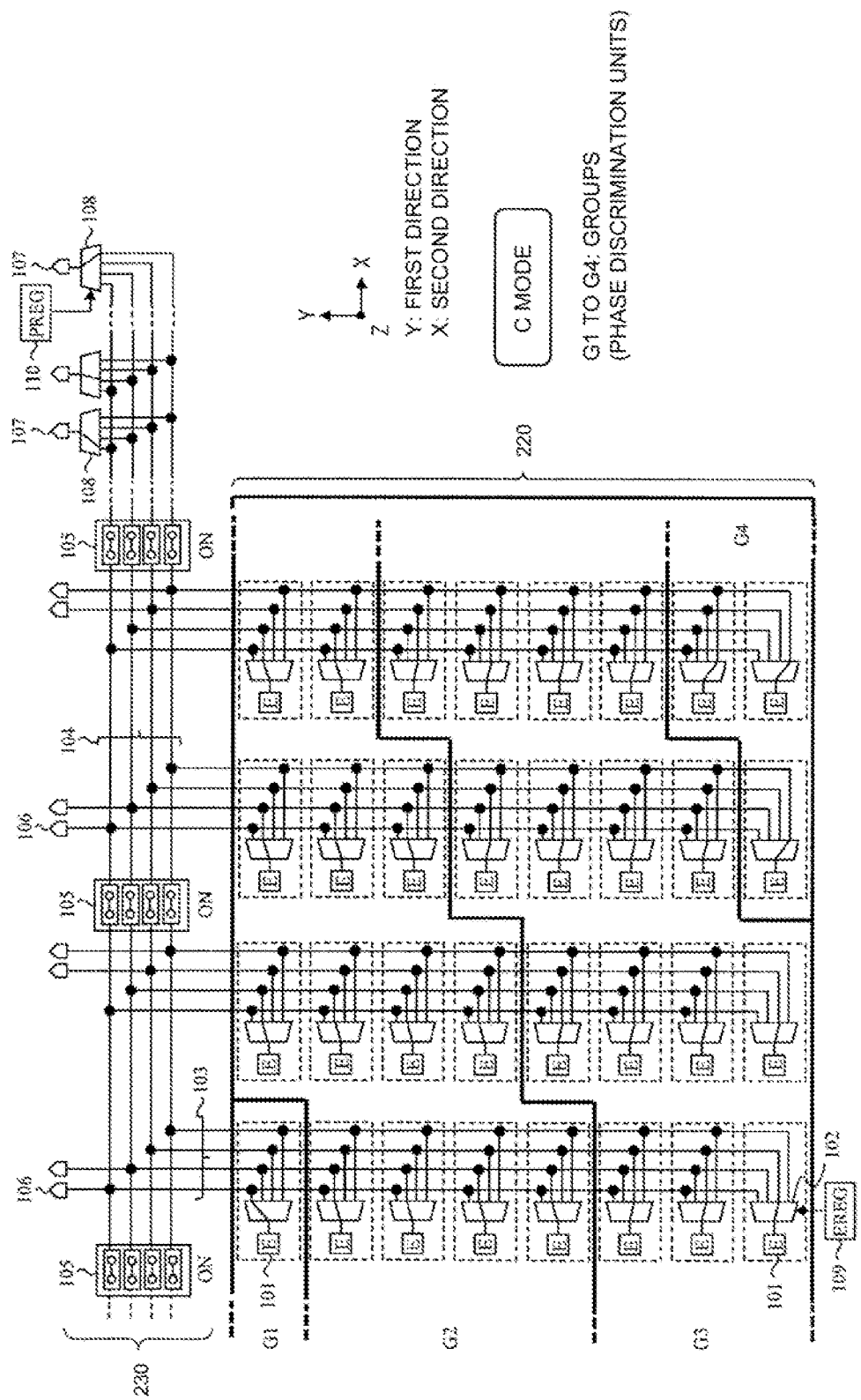
FIG. 4 shows an example of the circuit configuration of the probe of Embodiment 1, which is an example of the circuit status in the continuous wave Doppler mode (C mode)

FIG. 4 shows the circuit configuration and the like of the two-dimensional array ultrasound probe 2 of Embodiment 1, and shows an example of the circuit status in the continuous wave Doppler mode (C mode). FIG. 4 shows an example of continuous wave Doppler-based phase discrimination of a reception signal. A circuit like that in FIG. 4 is implemented in the IC in the probe 2. The probe 2 is roughly divided into the array area 220 and the outer area 230. In the array area 220 of the probe 2, reception circuits 101, a plurality of the first multiplexers 102, a plurality of the first wires 103, and the like in a plurality of (M) transducer channels 201 are implemented in a two-dimensional array. In the outer area 230 of the array area 220, second wires 104, a plurality of the switches 105, a plurality of the second multiplexers 108, a plurality of the first output ports 107, and a plurality of the second output ports 106 are implemented.

In this example, the vertical direction in the drawing corresponding to the direction of the columns of transducers 3 is the first direction (direction Y), and the horizontal direction in the drawing corresponding to the direction of the rows of transducers 3 is the second direction (direction X), Note that because of the relative relationship, the ultrasound probe disclosed in this description is achieved even if the rows and columns are swapped. FIG. 4 schematically shows a part of the entire array of the probe 2. Although there are a large number of (M) transducer channels 201, FIG. 4 only shows an (8×4) array. If the number of rows extending in the direction Y of the array is m1 and the number of columns extending in the direction X is m2, then m1×m2=M.

The reception circuit 101 of the transducer channel 201 for each transducer 3 is connected to a plurality of signal lines in the first wire 103 via the first multiplexer 102. The first multiplexer 102 provided for each transducer 3 is connected to a first register 109. Each reception circuit 101 is connected to one of the signal lines in the first wires 103 according to the switching or selected state by the first multiplexer 102. The first multiplexer 102 is a 1:n-connecting multiplexer that can connect one transducer 3 to a plurality of signal lines in the first wire 103 and switch the output signal line, and in this example, n=4. Switching and selection by each first multiplexer 102 is controlled using the control information set by the control logic circuit 9 to the first register 109. Note that 1:n means one input and a plurality of (n) outputs.

Each of the first wires 103 is a plurality of signal lines extending in the first direction for each column of transducers 3. A plurality of the first wires 103 are aligned in the direction X. The number of signal lines in the first wire 103 for each column of transducers 3 is greater than or equal to the number of phases of the continuous wave Doppler reception signal in the C mode. In this example, this first wire 103 is four signal lines supporting four phases. The four signal lines of the first wire 103 are associated with the respective four phases in phase discrimination of continuous wave Doppler reception signals. Example groups corresponding to phase discrimination units are shown as groups G1 to G4. Each group is associated with the corresponding phase. For example, the reception circuit 101 of the first group G1 is connected to the first signal line that is leftmost in the first wire 103 via the first multiplexer 102. The reception circuit 101 of the second group G2 is connected to the second signal line that is the second from the left in the first wire 103 via the first multiplexer 102.

The plurality of first wires 103 corresponding to a plurality of columns are connected to the second wire 104 in the outer area 230. Each of the second wires 104 is a plurality of signal lines extending in the second direction (direction X) in the form of one row. The second wire 104 includes a plurality of (four) signal lines corresponding to the number of (four) signal lines of the first wire 103. The plurality of signal lines in each first wire 103 and second wire 104 are associated with a plurality of phases of the continuous wave Doppler reception signal. For example, the leftmost first signal line in the first wire 103 is connected to the uppermost first signal line in the second wire 104 and is associated with the first phase. The second signal line of the first wire 103 is connected to the second signal line that is the second from the top of in the second wire 104, and is associated with the second phase.

Figure 5:
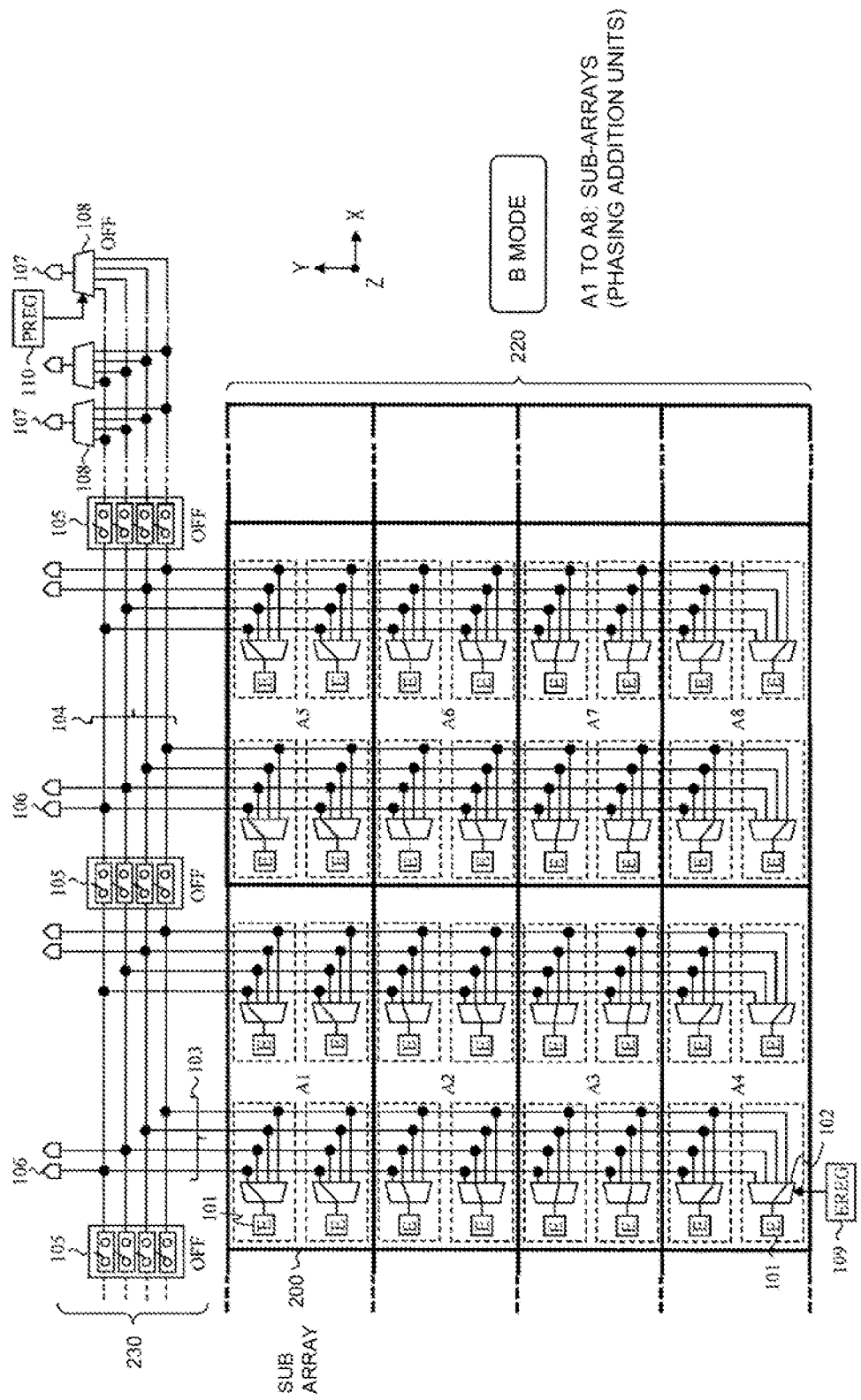
FIG. 5 shows an example of the circuit status in the imaging mode (B mode) in the example of the circuit configuration of the probe of Embodiment 1.

In the second wire 104, a plurality of columns of first wires 103 are divided into a plurality of parts by a plurality of the switches 105. In this example, every two columns of first wires 103 are grouped together between the switches 105. In the B mode, the switches 105 are used to electrically separate and disconnect a plurality of reception signals from a plurality of transducer channels 201 (corresponding first wires 103) into sub-arrays 200 serving as phasing addition units (FIG. 5). In the B mode, all the switches 105 are brought into the off state according to switching control by the control logic circuit 9. Hence, a plurality of first wires 103 are separated into groups of sub-arrays 200 serving as phasing addition units. In the C mode, as shown in the drawing, all the switches 105 are brought into the on state according to switching control by the control logic circuit 9. Hence, the four signal lines in the second wire 104 are electrically connected to each other from end to end of the array with reference to the direction X (not shown in the drawing). In addition, a group corresponding to a phase discrimination unit is connected to each signal line of the second wire 104.

A plurality of (four) second output ports 106 corresponding to the number of (four) signal lines of the first wire 103 and the second wire 104 are connected to the second wire 104 for each part between the switches 105. A plurality of (four) second output ports 106 are connected to the plurality of (four) signal lines of the second wire 104, respectively. These second output ports 106 are used in the B mode, not in the C mode.

In the second wire 104 in a part of the outer area 230, a plurality of first output ports 107 are connected via a plurality of second multiplexers 108. The first output ports 107 are output ports for continuous wave Doppler reception signals in the C mode. The number of first output ports 107 to be provided is at least a number corresponding to the number of phases (for example, four) of phase discrimination, or more. A second register 110 is connected to the second multiplexer 108 provided for each first output port 107. Each first output port 107 can select and output a signal having a target phase from the four signal lines corresponding to the four phases of the second wire 104, according to the switching or selected state in the second multiplexer 108 under control by the control logic circuit 9. The second multiplexer 108 is an n:1-connecting multiplexer that can connect a plurality of signal lines in the second wire 104 to the first output port 107 and switch the output signal line, and in this example, n=4. In each second multiplexer 108, the switching or selected state is controlled using the control information set by the control logic circuit 9 for the register 110, and one of the signal lines of the second wire 104 is connected as au output source.

Under control by the control device 8 of the main unit 5, the control logic circuit 9 sets information for control on the corresponding multiplexer and stores it in the first register 109 and the second register 110.

As described above, the probe 2 has a circuit configuration including a hierarchical switch consisting of a combination of a first multiplexer 102 provided for each transducer 3 and a second multiplexer 108 provided for each first output port 107 used in the C mode. It should be noted that a multiplexer is a switch in a broad sense. Such a circuit configuration can support two modes of reception operation: phasing addition in the B mode and phase discrimination in the C mode. With such a circuit configuration, the probe 2 can support two modes with fewer switches and wires than in the prior art, thereby reducing the circuit size and power consumption.

Beamforming is available in the C mode. Upon reception operation in the C mode, under control by the control device 8 of the main unit 5, the focus point of continuous wave Doppler reception (for example, the backflow position of a valve of the heart) is set for the control logic circuit 9. According to the setting, each transducer channel 201 of the probe 2 is given a setting as to which phase out of the four phases is assigned to it. In accordance with the setting, selected phase information is stored in the first register 109 from the control logic circuit 9. The selected phase information is control information indicating which signal line of the first wire 103 is selected as an output line by the first multiplexer 102. A corresponding phase is assigned to each signal line of the first wire 103 and second wire 104. According to the selected phase information in the first register 109, each first multiplexer 102 connects the corresponding reception circuit 101 to the signal line selected from the first wire 103.

Further, upon reception operation in die C mode, under control by the control device 8 of the main unit 5, a setting is made so that the selected phase of each first output port 107 is assigned to the control logic circuit 9 so that an equal number of transducers 3 (corresponding transducer channels 201) can be connected to each first output port 107 used in the C mode. According to this setting, control information for assigning the selected phase of each first output port 107 from the control logic circuit 9 is stored in the second register 110. This selected phase assignment information indicates which phase signal line of the second wire 104 is selected as the output line by the second multiplexer 108. According to the selected phase assignment information, the second multiplexer 108 establishes a connection to the signal line of selected phase from the second wire 104. Correspondingly, each first output port 107 outputs the reception signal of the selected phase.

Based on this setting, a plurality of transducer channels 201 are classified into a plurality of phase discrimination groups G1 to G4 as shown in the example in the drawing, and each first output port 107 outputs a reception signal having the phase of the corresponding group.

Equalizing the number of transducer channels connected to each first output port 107 refers to avoiding difference and inequality by making the numbers as equal or close as possible. For example, the leftmost first output port 107 outputs the reception signal of the phase discrimination-based first group G1 connected to the first signal line of the second wire 104. The first output port 107 that is the second from the left outputs the reception signal of the phase discrimination-based second group G2 connected to the second signal line of the second wire 104. Equalization refers to making the number of signals to be, for example, added representing each group between these first output ports 107, to be as equal as possible.

Note that in FIG. 4 which only shows a part of the transducer channels, the numbers of transducer channels belonging to the respective groups seem to be different, but there are actually more transducer channels and the number of transducer channels for each group connected to each first output port 107 can be equalized. Suppose that the total number of first output ports 107 is 100, and the numbers of reception signals for the respective groups G1 to G4 are g1 to g4, respectively, for example. In the case of the (8×4) transducer channel array shown in the example in FIG. 4, the ratio of the number of reception signals of the groups (g1:g2:g3:g4) is 1:13:15:3. The total number of first output ports 107, 100, is divided according to this ratio. Thus, the ratio of the numbers of first output ports 107 assigned to the respective groups is, for example, 4:40:46:10. For instance, one reception signal of the first group G1 uses four first output ports 107, and 13 reception signals in the second group G2 use 40 first output ports 107. For each first output port 107, the reception signals of about four transducer channels are combined into one.

In this way, equalizing the number of transducer channels connected to each first output port 107 allows the image obtained from the reception signals in the t rain unit 5 in the C mode to be a preferred continuous wave Doppler image with less unnecessary unevenness of brightness due to dependence on the focus point (associated inequality).

As in the example of FIG. 4, upon reception operation in the C mode, phase discrimination discriminates a plurality of continuous wave Doppler reception signals of a plurality of transducer channels 201 of the array area 220 into four groups G1 to G4 corresponding to four phases. The signals are then divided as reception signals into phase groups and output from different first output ports 107. In the example shown in the drawing, the four groups G1 to G4 are divided into steps in the array. This example correspond, to a Fresnelling-like phase distribution. For the phase discrimination, the number of phases is not limited to four.

In the C mode, a plurality of reception signals output from a plurality of first output ports 107 (corresponding to the plurality of output ports 6 in FIG. 2) are transmitted to a plurality of input ports 7 of the main unit 5 through the cable 4 and then processed in the respective reception circuits 70. According to the plurality of reception signals, the reception circuits 70 in the main unit 5 demodulate the signals to the baseband by mixing with a phase-adjusted continuous wave frequency signal, and add the demodulated reception signals together into fewer reception signals. Through such operation, phasing addition is performed in the main unit 5. This operation corresponds to delaying and addition performed in the micro delay circuit 36 in FIG. 3.

As described above, in the circuit configuration of the probe 2 of Embodiment 1, phasing addition by delaying is not necessary for the reception signals for each transducer 3 in the circuit inside the probe 2, which eliminates the need for use or implementation of active circuits such as amplifier circuits and delay circuits. In the circuit inside the probe 2, the aforementioned phase discrimination is performed as preprocessing for demodulation and phasing addition in the main unit 5. The aforementioned phase discrimination can be achieved with a hierarchical switch structure using the aforementioned multiplexers, for example; i.e., only passive circuits. This contributes to a reduction in the power consumed by the IC in the probe 2 for the reception operation in the C mode.

[1-5. B Model]

FIG. 5 shows an example of the circuit status in the B mode in the circuit configuration of the same probe 2 as in FIG. 4. FIG. 5 shows an example of phasing addition of reception signals in the B mode. Upon reception operation in the B mode, a plurality of the first wires 103 are divided into a plurality of the sub-arrays 200 as phasing addition units. In this example, a (2×2=4) matrix of transducer channels 201 is used as one sub-array 200. For example, a (8×2) matrix of transducer channels 201 is divided into four sub-arrays 200 (for example, A1 to A4) in the Y direction, and is connected to the portion between the switches 105 of the second wire 104. Similarly, a plurality of such four sub-arrays 200 aligned in the Y direction is aligned in the direction X.

In each sub-array 200, according to the selected state in each first multiplexer 102, the reception circuits 101 of the plurality of (four) transducer channels 201 are connected to, out of a plurality of (four) signal lines of the first wire 103, different signal lines depending on each sub-array 200. Hence, they are separated into sub-arrays 200. For example, in the sub-array A1, the reception circuits 101 of the four transducer channels 201 are all connected to the leftmost first signal line of the first wire 103 through the selected state in the respective first multiplexers 102. In the sub-array A2, the four reception circuits 101 are all connected to the second signal line that is the second line from the left of the first wire 103.

Upon reception operation in the B mode, the switches 105 are turned off and the second output ports 106 are used. The first output ports 107 are separated by the switches 105 and are therefore not used. Since the switches 105 are in the off state, the four signal lines of the second wire 104 are connected to the second output ports 106 used for the B mode, respectively.

The four reception signals of one sub-array 200 (e.g., sub-array A1) are connected to the same signal line (e.g., the uppermost first signal line) in a part between the switches 105 in the second wire 104 through the respective signal lines of the first wire 103 and output from the second output ports 106 connected to these signal lines. In particular, the four reception signals of one sub-array 200 are phasing-added through such wires into ono reception signal, which is then output from the second output port 106. Similarly, looking at the four sub-arrays 200 aligned in the direction Y, the reception signals for each sub-array 200 are separated through the separate signal lines of the first wire 103 and second wire 104 and output from the respective separate second output ports 106. Looking at the adjacent two columns aligned in the direction X connected to a part between the switches 105, the separate reception signals of the four sub-arrays 200 (for example, A1 to A4) are output from the four second output ports 106.

In the circuit status shown in FIG. 5, in one sub-array 200 with four transducer channels 201, phasing addition is performed in the following manner. The pulse reception signals in the B mode are delayed in the reception circuit 101 (the micro delay circuit 36 in FIG. 3). In phasing achieved using this delay, the phases of the reception signals are coherently made equal among the four transducer channels 201 of the sub-array 200. After that, the four reception signals are added into as one reception signal through the first multiplexers 102, first wire 103, and second wire 104.

In this way, the reception signals obtained after phasing addition is performed for each sub-array 200 are output from the second output ports 106.

The control information stored in the first register 109 in the B mode shown in FIG. 5 is not the selected phase information observed in the C mode described above, but information indicating which sub-array 200 or phasing addition unit each transducer channel 201 belongs to. For this reason, when the configuration of each sub-array 200 is fixed, the control information in the first register 109 is determined for each transducer 3 independently of the focus position of beamforming. Therefore, the control information in this case is fixedly preset by the control device 8 and the control logic circuit 9 and does not need to be calculated and set each time. Alternatively, the sub-array 200 configuration may be changed each time. If that is the case, the control information stored in the first register 109 is calculated and set each time by the control device 8 and the control logic circuit 9. For example, two adjacent sub-arrays 200 aligned in the direction Y shown in the drawing are controlled to be connected to the same signal line so that they can be combined into one sub-array.

Advantageous Effects and the Like

As described above, the two-dimensional array ultrasound probe of Embodiment 1 contributes to accomplishment of an apparatus having an advanced function that enables reception operation in at least two modes such as a continuous wave Doppler mode (C mode) and another imaging mode (B mode), and a reduction in its circuit size and power consumption. According to Embodiment 1, the circuit configuration of the circuit of the two-dimensional array ultrasound probe can be accomplished with fewer switches, wires, and the like than in the prior art (for example, the matrix switch in JP 2011-142931 A). In addition, in this circuit configuration, connections between the transducer channels 201 of the array and the channels of the main unit 5 can be established only through mainly passive circuits such as switches and multiplexers, thereby minimizing use of active circuits such as amplifiers and delay circuits. Consequently, with this circuit configuration, reception operation can be achieved at low power consumption and low noise in the C mode. Furthermore, in this circuit configuration, the number of transducer channels connected to each output port of the array can be equalized in the C mode. This provides suitable continuous wave Doppler images with less unnecessary unevenness of brightness due to dependence on the focus point for beamforming.

Embodiment 2

A two-dimensional array ultrasound probe of Embodiment 2 of the ultrasound probe disclosed in this description will be described with reference to FIGS. 6 and 7. The basic configuration of Embodiment 2 and the like is the same as that of Embodiment 1, and the components of Embodiment 2 and the like different from Embodiment 1 will be mainly described below. Embodiment 2 corresponds to a modification of the circuit configuration of the probe 2 of Embodiment 1. Both embodiments have the same effect of reducing the circuit size and power consumption as compared with the prior art example.

In Embodiment 1 (see FIG. 4, for example,) described above, the first output ports 107 for the C mode and the second output ports 106 for the B mode are separately provided. In contrast, Embodiment 2, in which there is no distinction between the first output ports 107 and the second output ports 106, includes common outputs that can be used in any mode as the output ports of the probe 2 so that the same output ports can be used regardless of whether or not it is in the C mode. As a result, in Embodiment 2, the number of output ports provided in the probe 2 can be reduced to a smaller number, and the number of cables 4 can be reduced accordingly.

[2-4. C Mode]

Figure 6:
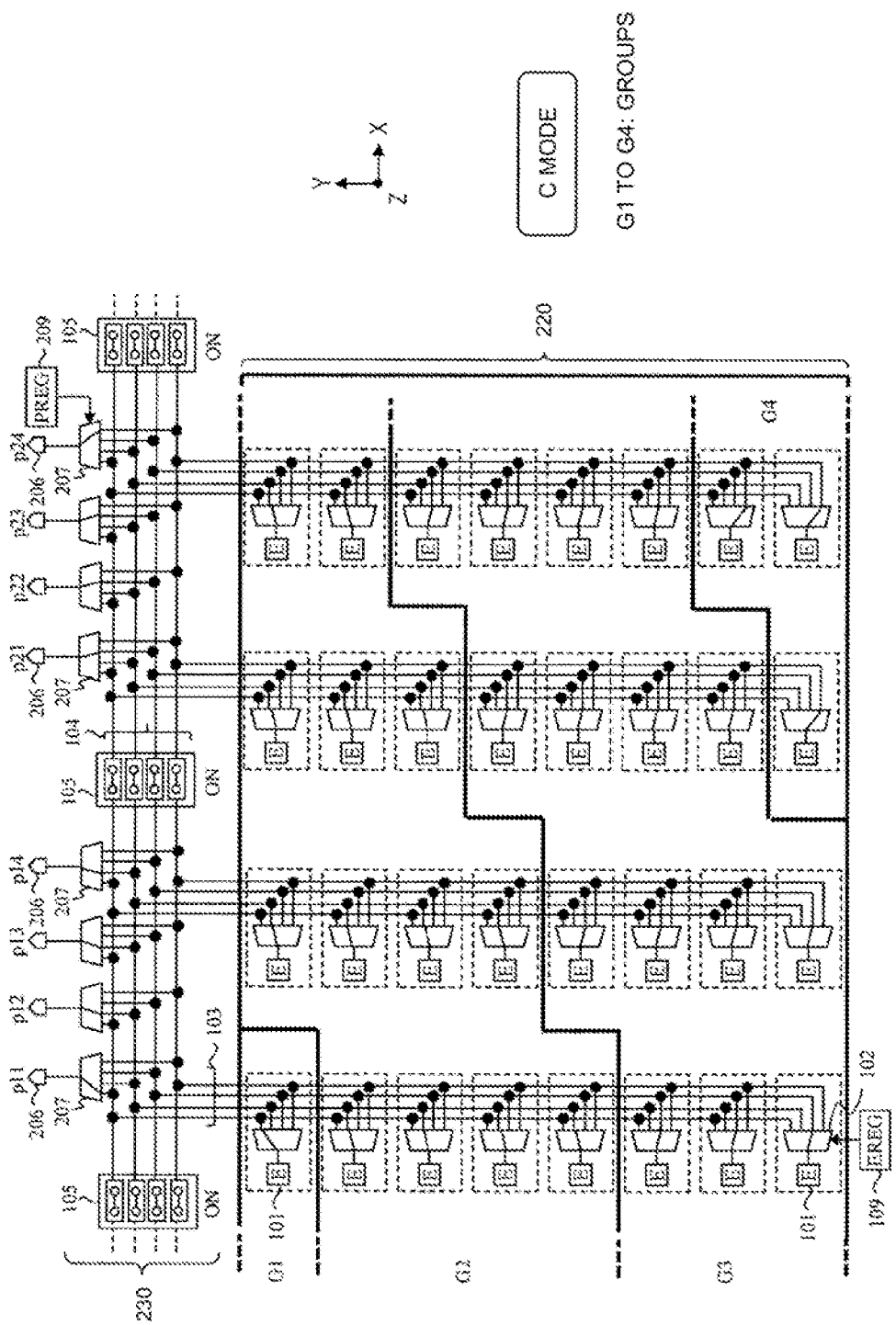
FIG. 6 shows an example of the circuit status in the C mode in the example of the circuit configuration of a probe of Embodiment 2.

FIG. 6 shows an example of phase discrimination as an example of the circuit status in the C mode in the circuit configuration of the probe 2 in Embodiment 2. In the probe 2 of Embodiment 2, the configuration in which the reception circuit 101 of each transducer channel 201 is connected to the first wire 103 via the first multiplexers 102 in the array area 220, and the configuration in which they are connected to the second wire 104 in the outer area 230 are the same as those in Embodiment 1. The selected phase information is stored as control information in the first register 109 connected to the first multiplexers 102.

In the C mode, in the outer area 230, the second wire 104 is electrically connected from end to end of the array when a plurality of switches 105 in the on state are connected thereto. In the outer area 230, a plurality of output ports 206 are provided to the second wire 104 for each portion between the switches 105 through a plurality of multiplexers 207. The output ports 206 translate into common output ports which are used in common in two modes. One multiplexer 207 is provided for each output port 206. This multiplexer 207 is a n:1-connecting multiplexer that connects a plurality of (four) signal lines in the second wire 104 to an output port 206, and in this example, n=4. Each multiplexer 207 is connected to a control register 209. In the C mode, each register 209 stores selected phase assignment information about the output port 206.

In the example shown in FIG. 6, two columns aligned in the direction X in the array area 220 are connected to the portion between the switches 105 of the second wire 104. In this area, four output ports 206 are connected to the four signal lines of the second wire 104 via four multiplexers 207.

In the example shown in FIG. 6, as in the aforementioned case (FIG. 4), four separate groups G1 to G4 corresponding to four phases are shown as an example of phase discrimination. For example, the reception signals of the transducer channels 201 in the group G1 pass through the first signal line of the first wire 103, the first signal line of the second wire 104, and, out of the four multiplexers 207 in the portion between the respective switches 105, the leftmost multiplexer 207, and are output in the form of one reception signal per each portion from, out of the four output ports 206, the leftmost output port 206 (p11), for example. Similarly, the reception signals of the transducer channels 201 in the group G2 pass through the second signal line of the first wire 103, the second signal line of the second wire 104, and, out of the four multiplexers 207 in the portion between the switches 105, the second multiplexer 207 from the left, and are output in the form of one reception signal per each portion from, out of the four output ports 206, several output ports 206 (p12, p13, and p14), for example.

Also in Embodiment 2, as in Embodiment 1, the number of transducer channels connected for each output port 206 is equalized upon reception operation in the C mode involving beamforming.

[2-2. B Model]

Figure 7:
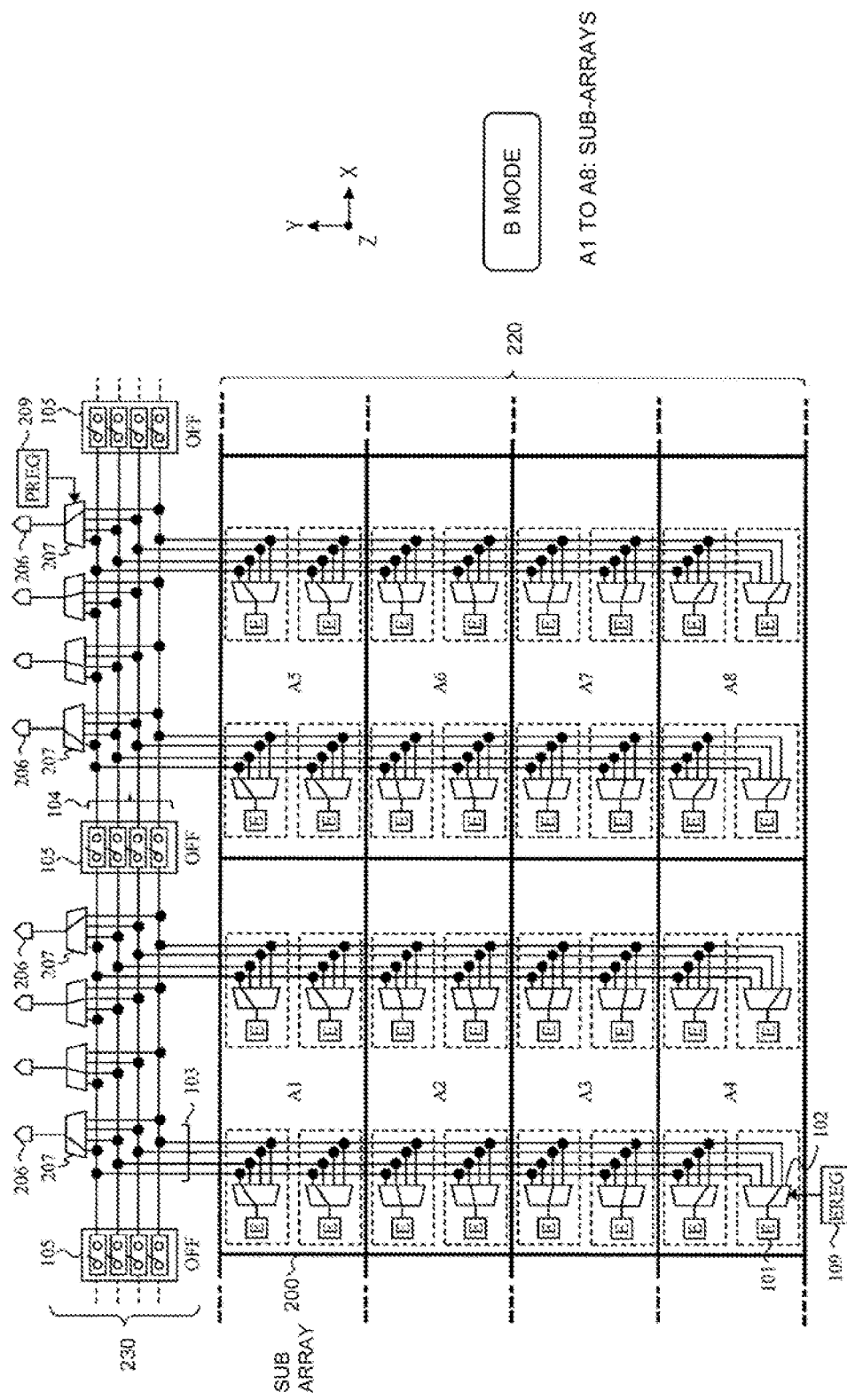
FIG. 7 shows an example of the circuit status in the B mode in the example of the circuit configuration of the probe of Embodiment 2.

FIG. 7 shows an example of sub-arrays 200 and the like as an example of the circuit status in the B mode in the circuit configuration of the probe 2 in Embodiment 2. In the B mode, the second wire 104 in the outer area 230 must be separated between phasing addition units, and all the connected switches 105 are therefore in the off state. Each sub-array 200, which is a phasing addition unit, is the same as in the example of Embodiment 1 (FIG. 5), and is (2×2=4) matrix of transducer channels 201.

In the B mode, the multiplexer 207 for each output port 206 selects which signal line from the second wire 104 is used as an output source to the output port 206 according to the information in the register 209. The information stored in the register 209 is information indicating which signal line of the second wire 104 is selected in accordance with the sub-array 200. In Embodiment 2, based on such a hierarchical switch structure consisting of a combination of first multiplexers 102 and multiplexers 207, a determination is made as to into which sub-array 200 the plurality of reception signals of the plurality of transducer channels 201 are divided and from which output port 206 they are output. According to control, in the portion between every two columns of switches 105, the output of added reception signals of each sub-array 200 is output from the corresponding output ports 206 out of the four output ports 206.

Advantageous Effects and the Like

As described above, the two-dimensional array ultrasound probe in Embodiment 2 can produce the same advantageous effects as Embodiment 1 and can also reduce the number of output ports provided in the probe 2 to a smaller number, and can accordingly reduce the number of cables 4.

Embodiment 3

The two-dimensional array ultrasound probe of an Embodiment 3 of the ultrasound probe disclosed in this description will now be described with reference to FIGS. 8 and 9. Embodiment 3 is a modification of Embodiment 2. The circuit configuration of the probe 2 of Embodiment 3 shown in FIG. 8 and the like includes output ports 307 which are common output ports as in Embodiment 2, and a partial wire to be used from the aforementioned second wire 104 is separated in the C mode and B mode. This reduces the series-connection resistance of the path of the continuous wave Doppler reception signal.

In Embodiments 1 and 2 described above, a plurality of switches 105 for separating the phasing addition units are inserted in the second wire 104 in the outer area 230 of the array. With such a circuit configuration, the on-resistance of each switch 105 may cause a decrease in signal amplitude, variations, and an increase in thermal noise. In particular, in the C mode, when the reception signals from the transducers 3 are output only through passive circuits without using the aforementioned amplifiers and the like, the aforementioned advantages can be produced, but signal amplification by amplifiers and impedance conversion cannot be achieved in the probe 2. If that is the case, the on-resistance of each switch 105 may have a big impact. For example, when the transducer 3 leftmost in the direction X in the array area 220 and the output port rightmost in the direction X in the outer area 230 are electrically connected to each other, the larger the two-dimensional array, the greater the number of series-connected switches 105 inserted in the related connection path. Accordingly, the second wire 104 inevitably has high resistance.

Figure 8:
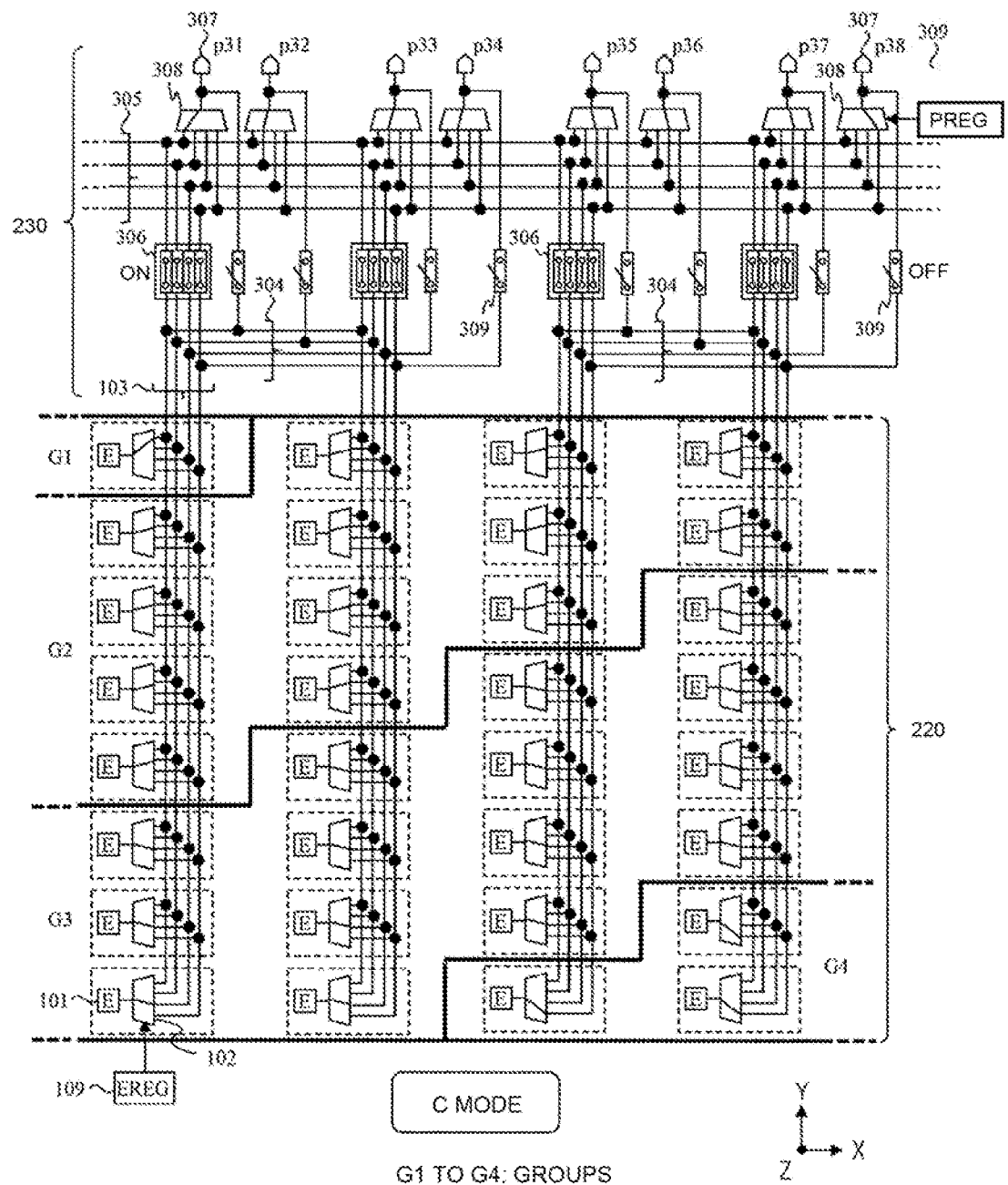
FIG. 8 shows an example of the circuit status in the C mode in the example of the circuit configuration of a probe of Embodiment 3.

For this reason, in the circuit configuration of the probe 2 of Embodiment 3, as shown in FIG. 8 and the like, the aforementioned second wire 104 in the outer area 230 has a circuit configuration in which a wire 304 used in the B mode and a wire 305 used in the C mode are separated. The wire 304 used in the B mode and extending in the direction X is connected to a plurality of first wires 103 of the array area 220. The wire 304 used in the B mode includes a plurality of signal lines for the respective signal lines of the first wire 103. The wire 304 used in the B mode is a plurality of wires separated according to the configuration of the sub-array 200 in the direction X. This wire is provided, for example, for every two columns. Further, in Embodiment 3, the wire 305 used in the C mode and extending in the direction X is connected to a plurality of first wires 103 in the array area 220 via switches 306.

[3-1. C Mode]

FIG. 8 shows an example of phase discrimination as an example of the circuit status in the C mode in the circuit configuration of the probe 2 in Embodiment 3. This probe 2 includes, in the outer area 230 of the array area 220, a wire 305 used in the C mode, wires 304 used in the B mode, switches 306, and switches 309. The first wire 103 in the outer area 230 is connected to the wire 304 used in the B mode and is connected to the wire 305 used in the C mode via switches 306. Although not shown in the drawing, switching of each switch is controlled according to the control signal from the control logic circuit 9.

The switch 306 is a switch provided for each column of transducers 3, and consists of a plurality of (four) switches provided respectively for a plurality of (four) signal lines for each first wire 103. In the C mode, the switches 306 are brought into the on state to use the wire 305 for the C mode. In the C mode, the switches 309 connecting the wire 304 used in the B mode to the output ports 307 is brought into the off state.

In the wire 305 used in the C mode, a plurality of output ports 307 are provided via a plurality of multiplexers 308 as in Embodiment 2. As in Embodiment 2, the output ports 307 are common output ports used in common in each mode. The multiplexer 308 for each output port 307 selects, as a signal output source, a signal line from the plurality of signal lines of the wire 305 used in the C mode according to control information set in the register 309, and outputs it to the output port 307. Also, a signal line is connected to each output port 307 without a multiplexer 308 therebetween, but through one switch 309 from one corresponding signal line of the wire 304 used in the B mode. Switches 309 provided are a plurality of (four) switches connected to the respective signal lines for every two columns of wires of the wire 304 used in the B mode.

Upon reception operation in the C mode, for example, the reception signals of the transducer channels 201 of the group G1 are transmitted from the first signal lint of the first wire 103 to the first signal line of the wire 305 used in the C mode through the switch 306 in the on state. Then, the reception signal of the first signal line is output from the selected output port 307 (for example, p31) according to the selected state of the multiplexer 308 according to the phase discrimination. Similarly, a plurality of reception signals of the group G2 are output from the selected output ports 307 (for example, p32, p33, and p34) via the second signal line of the first wire 103, the switches 306, the second signal line of the wire 305, and the multiplexers 308. Also in Embodiment 3, as in Embodiments 1 and 2, the number of transducer channels connected for each output port 307 is equalized.

[3-2. B Mode]

Figure 9:
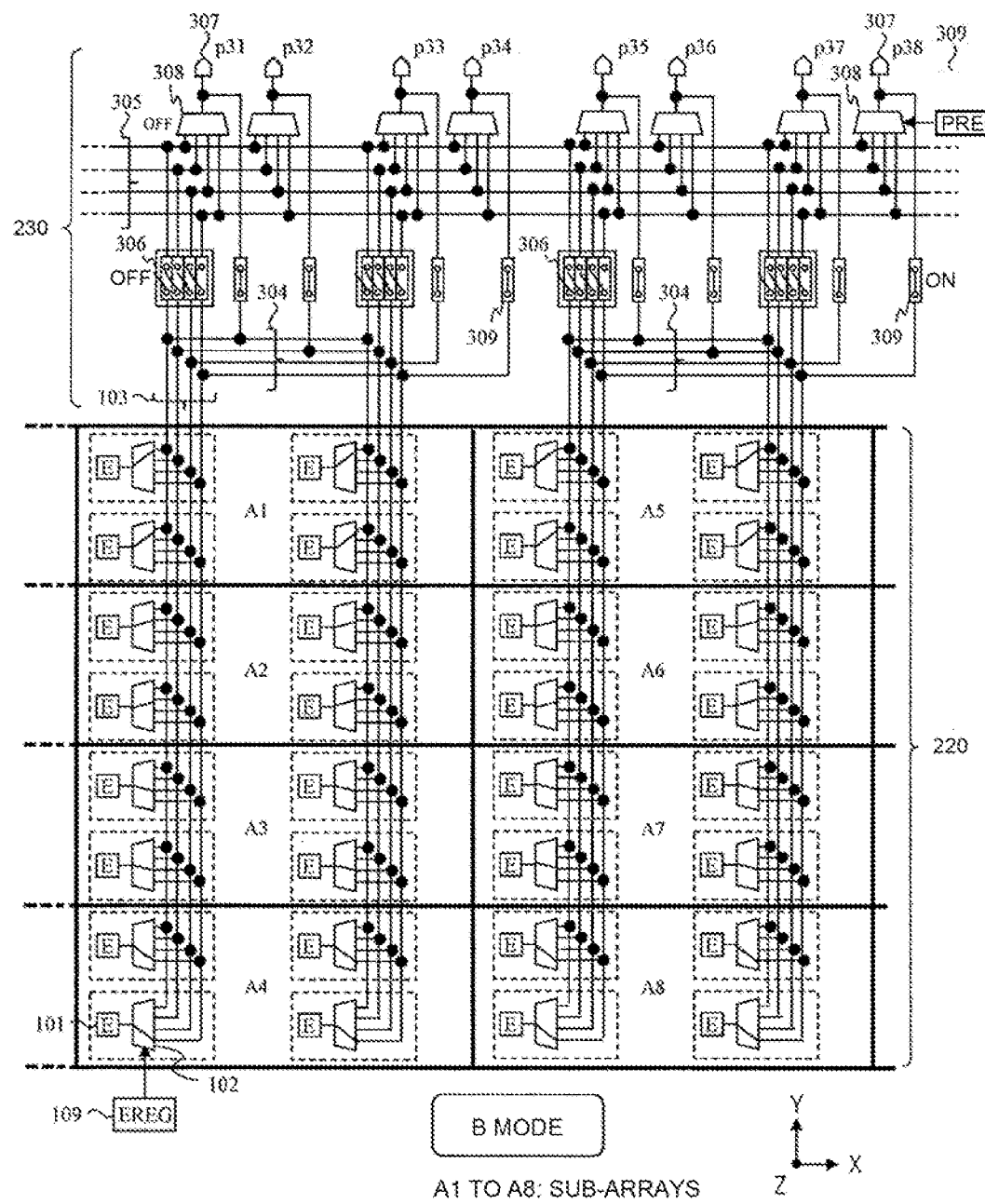
FIG. 9 shows an example of the circuit status in the B mode in the example of the circuit configuration of the probe of Embodiment 3.

FIG. 9 shows an example of sub-arrays 200 as an example of the circuit status in the imaging mode in the circuit configuration in Embodiment 3. In the B mode, the switches 306 are brought into the off state because the wire 305 for the C mode is not used. The switches 309 connected to the wire 304 used in the B mode is brought into the on state. The multiplexers 308 for the respective output ports 307 are also brought into the off state.

In this state in the B mode, according to control of the sub arrays 200, the reception signal of each transducer 3 passes through the first wire 103, the wire 304 used in the B mode, and the switch 309, and is output from the selected output port 307 as a reception signal that has been subjected to phasing addition for each sub-array 200, For example, the four reception signals of the four transducer channels 201 of the sub-array A1 pass through the first signal line of the first wire 103, the first signal line of the wire 304 used in the B mode, and the switch 309, and are output from the selected output port 307 (p31) as a reception signal that has been subjected to phasing addition.

Advantageous Effects and the Like

As described above, the two-dimensional array ultrasound probe in Embodiment 3 can produce the following advantageous effects as well as the same advantageous effects as Embodiments 1 and 2. In Embodiment 3, no switches 105 are inserted in the second wire 104 described above (for example, FIG. 6) in the wire 305 used in the C mode. In the circuit configuration of probe 2 of Embodiment 3, in the path of reception signals from a transducer 3 to an output port 307, on resistance is generated by the switch 306, but a plurality of switches 105 are not series-connected. Consequently, in this circuit configuration, the series-connection resistance in the path of the reception signals in the C mode can be reduced. Therefore, according to Embodiment 3, in terms of reception signal output, the concern about the influence on a decrease in signal amplitude, variations, an increase in thermal noise, and the like described above can be eliminated.

Embodiment 4

The two-dimensional array ultrasound probe of an Embodiment 4 of the ultrasound probe disclosed in this description will now be described with reference to FIGS. 10 and 11, Embodiment 4 is a modification of Embodiment 3, Embodiment 4 shows a circuit configuration in which the wire resistance generated upon continuous wave Doppler reception is effectively reduced by utilizing the surplus wiring. Embodiments 1 to 3 described above assume that, in terms of a relationship between the number of phases of the continuous wave Doppler reception signal in the C mode (referred to as the number of phases I) and the number of signal lines of the first wire 103 for each column of transducers 3 in the two-dimensional array of the probe 2 (referred to as the number of wires J), the number of phases I and the number of wires J are equal (I=J). These also assume that m the B mode, the number (the number of units K) of sub-arrays 200, which are phasing addition units, aligned in the first direction is 4, and the number of wires J is four accordingly. These numbers (I, J, and K) are, of course, not necessarily as in the aforementioned examples. In actual implementation, the number of phases I in the C mode and the number of units K in the B mode may be different. If they are different, the number of wires is determined according to the largest number among them.

Embodiment 4 assumes that the number of phases I of reception signals in the C mode is smaller than the number of units K of phasing addition units aligned in the first direction in the B mode (I<K). For example, there will be described the case where the number of phases X is 3 and the number of units K is 4 assuming that the sub-arrays 200 consisting of a (2×2=4) matrix of transducer channels 201 are phasing addition units. The number of wires J is made 4 according to the larger number of units K.

When the number of phases I is larger than the number of units K and the number of wires J, signal lines of the wire are left as surplus in the B mode. Further, as in Embodiment 4, when the number of units K in the B mode is larger than the number of phases I (I<K), signal lines of the wire are left as surplus in the C mode. For example, when, out of the four signal lines of the first wire 103 described above (the first to fourth signal lines from the left), three signal lines are used for outputting phase discrimination of three phases of continuous wave Doppler, the remaining one signal line is left as surplus. For this reason, in Embodiment 4, a mechanism that can effectively reduce the wire resistance by using a surplus wire in the C mode is added to the circuit configuration of Embodiment 3.

[4-1. C Mode]

Figure 10:
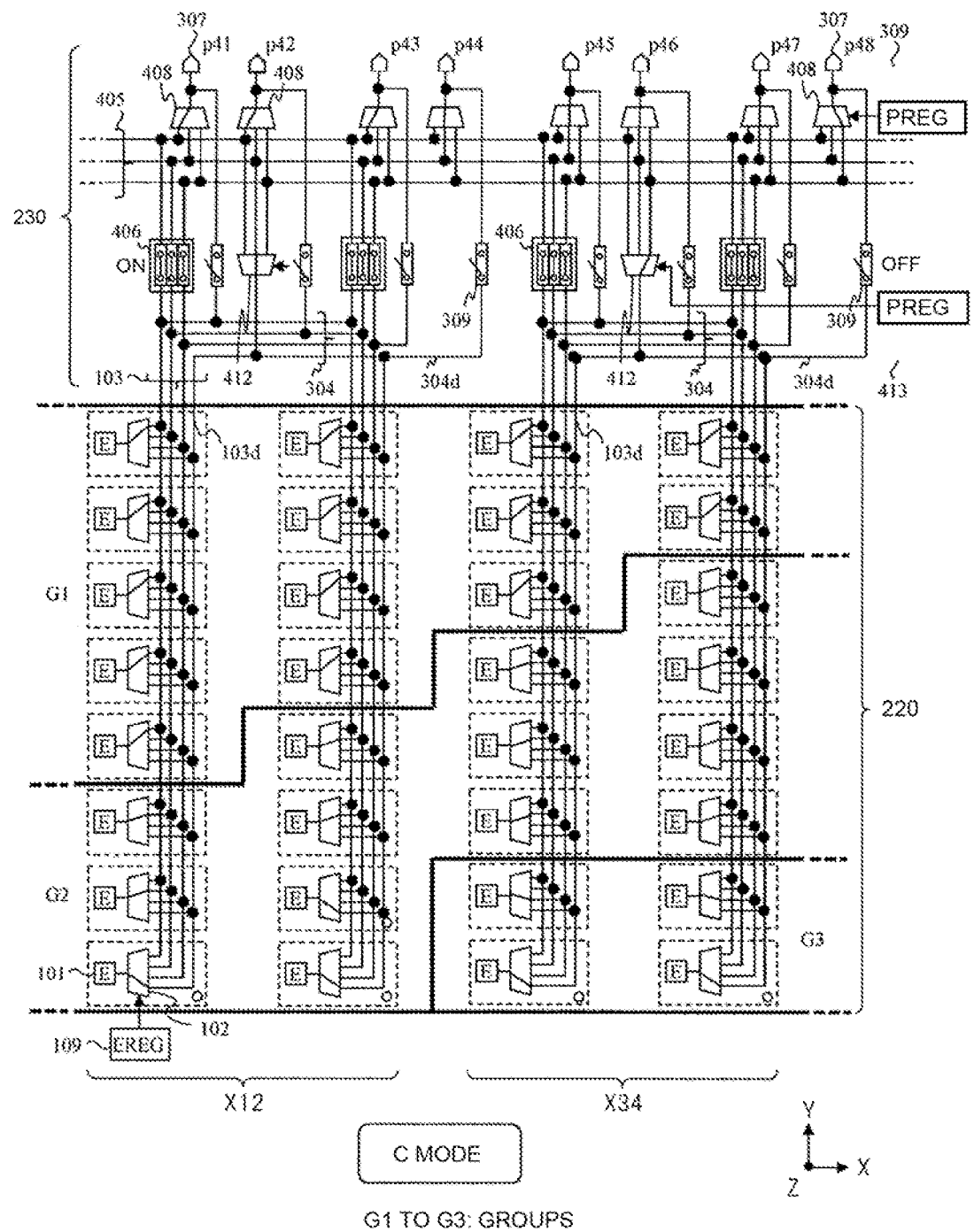
FIG. 10 shows an example of the circuit status in the C mode in the example of a circuit configuration of the probe of Embodiment 4.

FIG. 10 shows an example of phase discrimination as an example of the circuit status in the C mode in the circuit configuration of the probe 2 in Embodiment 4. In the circuit configuration of the probe 2 shown in FIGS. 10 and 11, in the outer area 230 of the array, multiplexers 412 and a register 413 are added to the circuit configuration of Embodiment 3. A wire 405 for the C mode has three signal lines corresponding to the number of phases instead of four lines. A multiplexer 408 for each output port 307 is, as an n:1-connecting multiplexer, not a 4:1-connecting multiplexer but a 3:1-connecting multiplexer. A switch 406 consists of three switches connected to three signal lines of the first wire 103. Each wire 304 for the B mode has four signal lines as described above, and one of them, the fourth signal line, is connected to one multiplexer 412. The multiplexer 412 is a 1:n-connecting multiplexer, particularly a 1:3-connecting multiplexer. The three outputs of the multiplexer 412 are connected to the three signal lines of the wire 405 for the C mode. Each multiplexer 408 has three inputs connected three signal lines of the wire 405, respectively.

Of the four signal lines of the first wire 103, the three signal lines from the left (first to third signal lines), for example, are used for three-phase discrimination. Of the four signal lines of the first wire 103, the rightmost signal line (fourth signal line) is a surplus wire 103*d*. The surplus wire 103*d* is connected to the wire 304 used in the B mode and is not connected to the wire 405 used in the C mode. In other words, the signal line 304*d*, which is the fourth signal line of the wire 304 used in the B mode, is a signal line extended from the surplus wire 103*d*.

A multiplexer 412 is a 1:3-connecting multiplexer located so as to provide a connection between the signal line 304*d* extended from the surplus wire 103*d* and three signal lines that support the number of phases of the wire 405 used in the C mode. Control information on the multiplexer 412 from the control logic circuit 9 is stored in the register 413. The control information stored in the register 413 is the information indicating selection of the wire used for the output of the multiplexer 412. In particular, in this circuit configuration, the surplus wire 103*d* can be connected to any of the three signal lines for three phases of the wire 405 used in the C mode, depending on the selected states in the first multiplexer 102 and the multiplexer 412. The reception signal of the transducer channel 201 connected to the surplus wire 103*d* is output to the selected signal line of the wire 405 used in the C mode, and then output from the output port 307 according to signal line selection by the multiplexer 408.

Upon reception operation in the C mode, three signal lines (first to third signal lines of the first wire 103 are connected to the wire 405 used in the C mode via the switch 406 in the on state. The three signal lines are assigned to three different phases (first phase, second phase, and third phase) of the continuous wave Doppler phase discrimination. In the phase discrimination example shown in FIG. 10, three groups G1 to G3 for phase discrimination are shown n the (8×4) matrix of transducer channels 201. For example, the group G1 is a group of the first phase, and the first multiplexer 102 is selecting the first signal line as the output line.

Here, when a large number of transducers 3 (corresponding transducer channels 201) are connected to the same wire, the first wire 103, the current flowing through the wire may increase and the wire resistance may have a big impact. Therefore, in Embodiment 4, the number of transducer channels connected to the same wire is reduced by utilizing the surplus wire 103d of the first wire 103, thereby reducing the impact of the wire resistance.

In the probe 2 of Embodiment 4, when there are many transducer channels 201 discriminated into the same phase at d aligned in the Y direction, the signal lines connected to the transducer channels 201 are distributed using the surplus wire 103d and the first multiplexer 102. In FIG. 10, for example, in the region X12 of two columns of transducers 3, the surplus wire 103d is assigned to, of three phases, a certain phase (for example, second phase) other than the phases of many transducer channels. In the region X34 of two other columns of transducers 3, under control, the surplus wire 103d is assigned to, of the three phases, another phase (for example, third phase) other than the phases of many transducer channels. The location of a transducer channel 201 connected to a surplus wire 103d is represented by a circle. The multiplexer 412 in the region X12 selects the second signal line corresponding to the second phase as the output line. The multiplexer 412 in the region X34, the third signal line corresponding to the third phase, is selected as the output line. With such control, the number of transducer channels aligned in the direction Y and connected to one signal line of the same wire can be reduced and the wire resistance can be effectively reduced.

The control device 8 of the main unit 5 calculates the control information set in the register 109 of the first multiplexer 102 for each transducer 3 and the register 309 of the multiplexer 408 for each output port 307, from the beamforming focus information, and the equalization of the number of transducer channels connected to each output port 307. At the same time, the control device 8 determines the phase to be assigned to the surplus wire 103d of each first wire 103, and transfers information on the phase assignment to the register 109 of the corresponding first multiplexer 102 and the register 413 of the multiplexer 412 and sets the information in them.

[4-2. B Mode]

Figure 11:
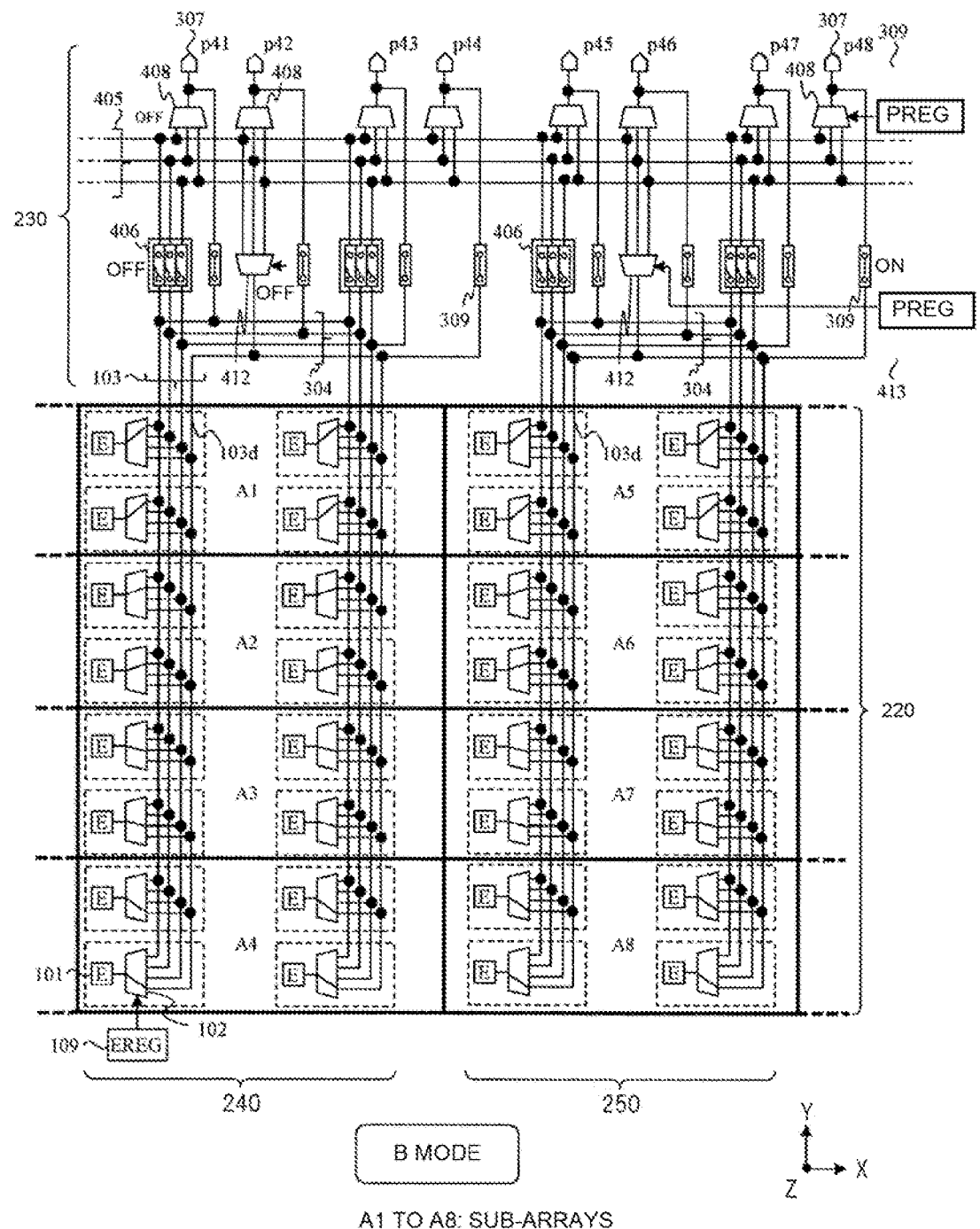
FIG. 11 shows an example of the circuit status in the B mode in the example of the circuit configuration of the probe of Embodiment 4.

FIG. 11 shows an example of sub-arrays 200 as an example of the circuit status in the B mode in the circuit configuration of the probe 2 in Embodiment 4. In the B mode, under control, the multiplexer 412 is brought into the off state and not used. Accordingly, in this state, the circuit shown in FIG. 11 is equivalent to the state of the circuit shown in FIG. 9. The portion of surplus wires 103d is used in the sub-arrays A4 and A8 in FIG. 11. The reception signals of the sub-arrays A4 and A8 are output from the output ports 307 through the surplus wires 103d and the switches 309 in the on state.

Although the embodiment of the ultrasound probe disclosed in this description has been described in detail, the ultrasound probe disclosed in this description is not necessarily as in the aforementioned embodiment, and various modifications can be made without departing from the spirit.

The invention claimed is:

1. An ultrasound probe including a plurality of transducers arranged in a two-dimensional array, wherein
   the ultrasound probe is enabled for ultrasonic reception operation of at least two modes: a first mode, which is a continuous wave Doppler mode, and a second mode, which is a mode other than the continuous wave Doppler mode, and
   a direction of one dimension of the two-dimensional array is a first direction, and a direction of the other dimension of the two-dimensional array is a second direction,
   the ultrasound probe comprising:
   a plurality of reception circuits, each reception circuit being provided for a corresponding one of the plurality of transducers;
   a plurality of first multiplexers, each first multiplexer being provided to be connected to a corresponding one of the plurality of reception circuits;
   a plurality of first wires, each of the first wires being provided to extend in the first direction and to be connected to plural ones of the first multiplexers;
   outside the two-dimensional array of the plurality of transducers, a second wire that is provided to be connected to the plurality of first wires and that extends in the second direction;
   switches that are provided to the second wire and that in the first mode are brought into an on state to close the switches and that in the second mode are brought into an off state to open the switches, the plurality of first wires separating into groups of sub-arrays serving as a plurality of phasing addition units corresponding to phasing addition of reception signals of the plurality of transducers;
   a plurality of second multiplexers that are connected to the second wire;
   a plurality of first output ports that are connected to the plurality of second multiplexers and used in the first mode to output continuous wave Doppler signals; and
   a plurality of second output ports that are connected to each region between the switches on the second wire and in the second mode, to output signals from the second wire.

2. The ultrasound probe according to claim 1, wherein for a plurality of reception signals of the plurality of transducers of the two-dimensional array,
   in the first mode, the first multiplexers, the switches, and the second multiplexers are controlled so as to achieve division of continuous wave Doppler reception signals into N number of groups corresponding to N number of phases according to phase discrimination, and
   in the second mode, the first multiplexers, the switches, and the second multiplexers are controlled so as to achieve division into the plurality of phasing addition units.

3. The ultrasound probe according to claim 2, further comprising:
   a first register for registering control information for controlling the plurality of first multiplexers; and
   a second register for registering control information for controlling the plurality of second multiplexers, wherein as control information, information for assigning a group for the phase discrimination is stored in the first register in the first mode, and information for assigning the phasing addition units is stored in the first register in the second mode, and as control information, information for assigning a phase to be output from the first output port is stored in the second register in the first mode.

4. The ultrasound probe according to claim 1, wherein in the first mode, a number of the plurality of transducers which are connected to each first output port is equalized under control, to permit an output image to have less unnecessary unevenness of brightness.

5. An ultrasound probe including a plurality of transducers arranged in a two-dimensional array, wherein
the ultrasound probe is enabled for ultrasonic reception operation of at least two modes: a first mode, which is a continuous wave Doppler mode, and a second mode, which is a mode other than the continuous wave Doppler mode, and
a direction of one dimension of the two-dimensional array is a first direction, and a direction of the other dimension of the two-dimensional array is a second direction, the ultrasound probe comprising:
a plurality of reception circuits, each reception circuit being provided for a corresponding one of the plurality of transducers;
a plurality of first multiplexers, each first multiplexer being provided to be connected to a corresponding one of the plurality of reception circuits;
a plurality of first wires, each of the first wires being provided to extend in the first direction and to be connected to plural ones of the first multiplexers;
outside the two-dimensional array of the plurality of transducers, a second wire that is provided to be connected to the plurality of first wires and that extends in the second direction;
switches that are provided to the second wire and that in the first mode are brought into an on state to close the switches and that in the second mode are brought into an off state to open the switches, the plurality of first wires separating into groups of sub-arrays serving as a plurality of phasing addition units corresponding to phasing addition of reception signals of the plurality of transducers;
a plurality of additional multiplexers having inputs that are connected to each region between the switches on the second wire; and
a plurality of output ports having inputs that are connected to outputs of the plurality of additional multiplexers and used in the first mode and the second mode to output signals from the outputs of the plurality of additional multiplexers.

6. The ultrasound probe according to claim 5, wherein for a plurality of reception signals of the plurality of transducers of the two-dimensional array,
in the first mode, the first multiplexers, the switches, and the additional multiplexers are controlled so as to achieve division of continuous wave Doppler reception signals into N number of groups corresponding to N number of phases according to phase discrimination, and
in the second mode, the first multiplexers, the switches, and the additional multiplexers are controlled so as to achieve division into the plurality of phasing addition units.

7. The ultrasound probe according to claim 6, further comprising:
a first register for registering control information for controlling the plurality of first multiplexers; and
a second register for registering control information for controlling the plurality of additional multiplexers, wherein
as control information, information for assigning a group for the phase discrimination is stored in the first register in the first mode, and information for assigning the phasing addition units is stored in the first register in the second mode, and
as control information, information for assigning a phase to be output from the output port is stored in the second register in the first mode, and information for assigning reception signals for the phasing addition units to be output from the output ports in the second mode.

8. The ultrasound probe according to claim 5, wherein in the first mode, a number of the plurality of transducers which are connected to each first output port is equalized under control, to permit an output image to have less unnecessary unevenness of brightness.

9. An ultrasound probe including a plurality of transducers arranged in a two-dimensional array, wherein
the ultrasound probe is enabled for ultrasonic reception operation of at least two modes: a first mode, which is a continuous wave Doppler mode, and a second mode, which is a mode other than the continuous wave Doppler mode, and
a direction of one dimension of the two-dimensional array is a first direction, and a direction of the other dimension of the two-dimensional array is a second direction, the ultrasound probe comprising:
a plurality of reception circuits, each reception circuit being provided for a corresponding one of the plurality of transducers;
a plurality of first multiplexers, each first multiplexer being provided to be connected to a corresponding one of the plurality of reception circuits;
a plurality of first wires, each of the first wires being provided to extend in the first direction and to be connected to plural ones of the first multiplexers;
outside the two-dimensional array of the plurality of transducers, an additional wire for the first mode that is provided to be connected to the plurality of first wires and that extends in the second direction;
outside the two-dimensional array and for the second mode, another wire which is provided to be connected to the plurality of first wires and that extends in the second direction;
a first switch that is provided between the additional wire for the first mode and said another wire for the second mode, and is brought into an on state to close the first switch in the first mode and brought into an off state to open the first switch in the second mode,
in the second mode, the first switch being in the off state and the plurality of first wires separating into groups of sub-arrays serving as a plurality of phasing addition units corresponding to phasing addition of reception signals of the plurality of transducers;
a plurality of second multiplexers that are connected to the additional wire for the first mode;
a plurality of output ports that are connected to the plurality of second multiplexers and the first switch and that are used in the first mode to output signals from the plurality of second multiplexers; and a second switch that is provided between said another wire for the second mode and each of the plurality of output ports, and is brought into the off state in the first mode and brought into the on state in the second mode, wherein in the second mode, outputs of the plurality of first multiplexers are passed through the plurality of output ports via the plurality of first wires and the second switch.

10. The ultrasound probe according to claim 9, wherein for a plurality of reception signals of the plurality of transducers of the two-dimensional array, in the first mode, the first multiplexers, the first switch, the second switch, and the second multiplexers are controlled so as to achieve division of continuous wave Doppler reception signals into N number of groups corresponding to N number of phases according to phase discrimination, and in the second mode, the first multiplexers, the first switch, the second switch, and the second multiplexers are controlled so as to achieve division into the plurality of phasing addition units.

11. The ultrasound probe according to claim 10, further comprising:

a first register for registering control information for controlling the plurality of first multiplexers; and a second register for registering control information for controlling the plurality of second multiplexers, wherein as control information, information for assigning a group for the phase discrimination is stored in the first register in the first mode, and information for assigning the phasing addition units is stored in the first register in the second mode, and as control information, information for assigning a phase to be output from the output port is stored in the second register in the first mode, and information for assigning reception signals for the phasing addition units to be output from the output ports in the second mode.

12. The ultrasound probe according to claim 9, wherein in the first mode, a number of the plurality of transducers which are connected to each first output port is equalized under control, to permit an output image to have less unnecessary unevenness of brightness.

13. The ultrasound probe according to claim 2, wherein ultrasonic beamforming is available in the first mode, and in the first mode, a phase of the reception signal of the reception circuit of each transducer calculated based on an ultrasonic beam focus point is set as a corresponding one of the plurality of phases.

14. The ultrasound probe according to claim 6, wherein ultrasonic beamforming is available in the first mode, and in the first mode, a phase of the reception signal of the reception circuit of each transducer calculated based on an ultrasonic beam focus point is set as a corresponding one of the plurality of phases.

15. The ultrasound probe according to claim 10, wherein ultrasonic beamforming is available in the first mode, and in the first mode, a phase of the reception signal of the reception circuit of each transducer calculated based on an ultrasonic beam focus point is set as a corresponding one of the plurality of phases.

16. The ultrasound probe according to claim 9, wherein signal lines of the first wire are connected to signal lines of said another wire for the second mode, and the ultrasound probe includes a third multiplexer that connects the signal lines of said another wire for the second mode to a plurality of signal lines of the additional wire for the first mode, and the signal lines of said another wire for the second mode are connected to a selected signal line of the additional wire for the first mode, according to a state of the third multiplexer.

* * * * *